US010369345B2

(12) United States Patent
Tallarida et al.

(10) Patent No.: US 10,369,345 B2
(45) Date of Patent: Aug. 6, 2019

(54) MEDICAL ACCESS PORT, SYSTEMS AND METHODS OF USE THEREOF

(71) Applicant: Versago Vascular Access, Inc., West Bridgewater, MA (US)

(72) Inventors: Steven J. Tallarida, Mansfield, MA (US); Richard P. Rodgers, Hudson, MA (US); John M. Butziger, East Greenwich, RI (US)

(73) Assignee: Versago Vascular Access, Inc., West Bridgewater, MA (US)

( * ) Notice: Subject to any disclaimer, the term of this patent is extended or adjusted under 35 U.S.C. 154(b) by 23 days.

(21) Appl. No.: 15/300,625

(22) PCT Filed: Mar. 31, 2015

(86) PCT No.: PCT/US2015/023590
§ 371 (c)(1),
(2) Date: Sep. 29, 2016

(87) PCT Pub. No.: WO2015/153611
PCT Pub. Date: Oct. 8, 2015

(65) Prior Publication Data
US 2017/0182303 A1 Jun. 29, 2017

Related U.S. Application Data

(63) Continuation-in-part of application No. 14/231,392, filed on Mar. 31, 2014, now Pat. No. 9,764,124.

(51) Int. Cl.
*A61M 39/02* (2006.01)
*A61M 39/22* (2006.01)
(Continued)

(52) U.S. Cl.
CPC ........ *A61M 39/0208* (2013.01); *A61M 5/158* (2013.01); *A61M 39/22* (2013.01);
(Continued)

(58) Field of Classification Search
CPC .. A61M 39/0208; A61M 39/04; A61M 5/158; A61M 2205/04; A61M 39/22;
(Continued)

(56) References Cited

U.S. PATENT DOCUMENTS 3,819,282 A  6/1974 Schultz
4,181,132 A  1/1980 Parks
(Continued)

FOREIGN PATENT DOCUMENTS

EP  1680174  7/2006
EP  2403431  1/2012
(Continued)

OTHER PUBLICATIONS

European Extended Search Report dated Nov. 27, 2017, issued in European Patent Application No. 15772648.0, 7 pages.
(Continued)

*Primary Examiner* — Lauren P Farrar
(74) *Attorney, Agent, or Firm* — Grossman Tucker Perreault & Pfleger PLLC

(57) ABSTRACT

A medical device comprising a subcutaneous access port having an access port body and at least one needle having a removable needle tip and a needle shaft defining a needle lumen; the at least one needle housed within the access port body, the at least one needle extendable and retractable relative to the access port body; and a needle shift mechanism operable such that the at least one needle is extendable from and retractable into the access port body at a plurality of positions of the access port body.

24 Claims, 24 Drawing Sheets

(51) Int. Cl.
*A61M 5/142* (2006.01)
*A61M 5/158* (2006.01)

(52) U.S. Cl.
CPC .......... *A61M 2005/14284* (2013.01); *A61M 2039/0226* (2013.01); *A61M 2039/0235* (2013.01); *A61M 2205/04* (2013.01)

(58) Field of Classification Search
CPC .. A61M 2039/0226; A61M 2039/0235; A61M 2005/14284
See application file for complete search history.

(56) References Cited

U.S. PATENT DOCUMENTS

| | | | |
|---|---|---|---|
| 4,190,040 A | 2/1980 | Schulte |
| 4,228,802 A | 10/1980 | Trott |
| 4,445,896 A | 5/1984 | Gianturco |
| 4,543,088 A | 9/1985 | Bootman et al. |
| 4,576,595 A | 3/1986 | Aas et al. |
| 4,673,394 A | 6/1987 | Fenton, Jr. et al. |
| 4,676,782 A | 6/1987 | Yamamoto et al. |
| 4,692,146 A | 9/1987 | Hilger |
| 4,710,167 A | 12/1987 | Lazorthes |
| 4,760,837 A | 8/1988 | Petit |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,919,653 A | 4/1990 | Martinez et al. |
| 4,929,236 A | 5/1990 | Sampson |
| 5,003,657 A | 4/1991 | Boiteau et al. |
| 5,006,115 A | 4/1991 | McDonald |
| 5,013,316 A | 5/1991 | Goble et al. |
| 5,041,098 A | 8/1991 | Loiterman et al. |
| 5,057,084 A | 10/1991 | Ensminger et al. |
| 5,084,015 A | 1/1992 | Moriuchi |
| 5,137,529 A | 8/1992 | Watson et al. |
| 5,203,771 A | 4/1993 | Melker et al. |
| 5,213,574 A | 5/1993 | Tucker |
| 5,215,530 A | 6/1993 | Hogan |
| 5,234,406 A | 8/1993 | Dransner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Tucker |
| 5,332,398 A | 7/1994 | Miller et al. |
| 5,337,756 A | 8/1994 | Barbier et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,423,334 A | 6/1995 | Jordan |
| 5,476,460 A | 12/1995 | Montalvo |
| 5,520,643 A | 5/1996 | Ensminger et al. |
| 5,522,817 A | 6/1996 | Sander et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A | 6/1997 | Wenner et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Tucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A | 12/1999 | Burbank et al. |
| 6,030,397 A | 2/2000 | Monetti et al. |
| 6,039,712 A | 3/2000 | Fogarty et al. |
| 6,113,572 A | 9/2000 | Gailey et al. |
| 6,190,352 B1 | 2/2001 | Haarala et al. |
| 6,213,973 B1 | 4/2001 | Eliasen et al. |
| 6,478,783 B1 | 11/2002 | Moorehead |
| 6,527,754 B1 | 3/2003 | Tallarida et al. |
| 6,962,577 B2 | 11/2005 | Tallarida et al. |
| 6,981,977 B2 | 1/2006 | Herweck et al. |
| 7,056,316 B1 | 6/2006 | Burbank et al. |
| 7,131,962 B1 | 11/2006 | Estabrook et al. |
| 7,351,233 B2 | 4/2008 | Parks |
| 7,452,354 B2 | 11/2008 | Bright et al. |
| 7,713,251 B2 | 5/2010 | Tallarida et al. |
| 7,803,143 B2 | 9/2010 | Tallarida et al. |
| 7,811,266 B2 | 10/2010 | Eliasen |
| 8,182,453 B2 | 5/2012 | Eliasen |
| 8,377,034 B2 | 2/2013 | Tallarida et al. |
| 8,409,153 B2 | 4/2013 | Tallarida et al. |
| 8,529,525 B2 | 9/2013 | Gerber et al. |
| 8,641,676 B2 | 2/2014 | Butts et al. |
| 8,656,929 B2 | 2/2014 | Miller et al. |
| 8,721,620 B2 | 5/2014 | Imran |
| 9,295,773 B2 | 3/2016 | Prosl et al. |
| 9,480,831 B2 | 11/2016 | Tallarida et al. |
| 10,238,851 B2 | 3/2019 | Butziger et al. |
| 2001/0016713 A1 | 8/2001 | Takagi et al. |
| 2001/0037094 A1 | 11/2001 | Adaniya et al. |
| 2002/0095122 A1 | 7/2002 | Shaffer |
| 2003/0109837 A1 | 6/2003 | McBride-Sakal |
| 2004/0097930 A1 | 5/2004 | Justis et al. |
| 2004/0158207 A1 | 8/2004 | Hunn et al. |
| 2005/0014993 A1 | 1/2005 | Mische |
| 2005/0085778 A1 | 4/2005 | Parks |
| 2005/0124980 A1 | 6/2005 | Sanders |
| 2005/0154373 A1 | 7/2005 | Deutsch |
| 2005/0171493 A1 | 8/2005 | Nicholls |
| 2005/0209619 A1* | 9/2005 | Johnson ................. A61B 17/34 606/167 |
| 2005/0267421 A1 | 12/2005 | Wing |
| 2006/0004325 A1 | 1/2006 | Hamatake et al. |
| 2006/0142705 A1 | 6/2006 | Halili |
| 2006/0178648 A1 | 8/2006 | Barron et al. |
| 2006/0224129 A1 | 10/2006 | Beasley et al. |
| 2006/0264988 A1 | 11/2006 | Boyle |
| 2007/0078432 A1 | 4/2007 | Halseth et al. |
| 2007/0100302 A1 | 5/2007 | Dicarlo et al. |
| 2007/0233019 A1* | 10/2007 | Forsell ............. A61M 5/14276 604/288.03 |
| 2007/0265595 A1 | 11/2007 | Miyamoto et al. |
| 2008/0039820 A1 | 2/2008 | Sommers et al. |
| 2008/0114308 A1 | 5/2008 | di Palma et al. |
| 2008/0243106 A1 | 10/2008 | Coe et al. |
| 2008/0262475 A1 | 10/2008 | Preinitz |
| 2011/0137288 A1* | 6/2011 | Tallarida ........... A61M 39/0208 604/513 |
| 2011/0160699 A1 | 6/2011 | Imran |
| 2011/0264058 A1 | 10/2011 | Linen et al. |
| 2011/0282285 A1 | 11/2011 | Blanchard et al. |
| 2011/0301652 A1 | 12/2011 | Reed et al. |
| 2011/0311602 A1 | 12/2011 | Mills et al. |
| 2012/0035585 A1 | 2/2012 | Kurrus et al. |
| 2012/0209180 A1 | 8/2012 | Gray et al. |
| 2012/0232501 A1 | 9/2012 | Eliasen |
| 2013/0218103 A1 | 8/2013 | Tallarida et al. |
| 2013/0226101 A1 | 8/2013 | Westcott |
| 2013/0231637 A1 | 9/2013 | Tallarida et al. |
| 2014/0102445 A1 | 4/2014 | Clement et al. |

(56) References Cited

U.S. PATENT DOCUMENTS

| | | | |
|---|---|---|---|
| 2015/0051584 A1 | 2/2015 | Korkuch et al. | |
| 2015/0273201 A1 | 10/2015 | Tallarida et al. | |
| 2016/0175560 A1 | 6/2016 | Tallarida et al. | |
| 2016/0175575 A1 | 6/2016 | Tallarida et al. | |
| 2017/0000995 A1 | 1/2017 | Tallarida et al. | |
| 2017/0014611 A1 | 1/2017 | Butziger et al. | |
| 2017/0173273 A1 | 6/2017 | Tallarida et al. | |
| 2018/0104465 A1 | 4/2018 | Tallarida et al. | |

FOREIGN PATENT DOCUMENTS

| | | |
|---|---|---|
| EP | 3322460 | 5/2018 |
| EP | 3233175 | 3/2019 |
| GB | 2502291 | 11/2013 |
| JP | 55-065009 | 5/1980 |
| JP | 9-509852 | 10/1997 |
| JP | 2009-273598 | 11/2009 |
| WO | 9701370 | 1/1997 |
| WO | 00/78231 | 12/2000 |
| WO | 0078231 | 12/2000 |
| WO | 2005025665 | 3/2005 |
| WO | 2005/094702 | 10/2005 |
| WO | 2007051563 | 5/2007 |
| WO | 2008126966 | 10/2008 |
| WO | 2009/148587 | 12/2009 |
| WO | 2015153976 | 10/2015 |
| WO | 2016/100868 | 6/2016 |
| WO | 2016/100945 | 6/2016 |

OTHER PUBLICATIONS

Office Action dated Nov. 30, 2017, issued in U.S. Appl. No. 15/210,268, 15 pages.
Preliminary Report on Patentability dated Jan. 25, 2018, issued in PCT Patent Application No. PCT/US2016/042272, 9 pages.
Office Action dated Aug. 31, 2017, issued in U.S. Appl. No. 14/974,851, 12 pages.
Search Report dated Nov. 8, 2017, issued in European Patent Application No. 15773029.2, 8 pages.
Office Action dated Feb. 26, 2018, issued in U.S. Appl. No. 14/974,851, 12 pages.
Office Action dated Mar. 27, 2018, issued in U.S. Appl. No. 14/975,638, 8 pages.
PCT International Search Report dated Nov. 21, 2001 issued in PCT Application No. PCT/US01/13749, 4 pages.
PCT Written Opinion dated Dec. 19, 2002 issued in PCT Application PCT/US01/13749, 5 pages.
PCT Preliminary Examination Report dated May 28, 2003 issued in PCT Application PCT/US01/13749,2 pages.
European Examination Report dated Jul. 30, 2003 issued in European Patent Application No. 99 964 086.5, 5 pages.
U.S. Office Action dated Aug. 27, 2003 issued in U.S. Appl. No. 09/842,458, 8 pages.
U.S. Office Action dated Dec. 23, 2003 issued in U.S. Appl. No. 09/842,458, 7 pages.
European Examination Report dated Mar. 9, 2004 issued in European Patent Application No. 99 964 086.5, 4 pages.
U.S. Notice of Allowance dated Oct. 15, 2004 issued in U.S. Appl. No. 09/842,458, 7 pages.
Australian Examination Report dated Jan. 21, 2005 issued in Australian Patent Application No. 2001257388, 2 pages.
U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 4 pages.
European Examination Report dated Mar. 30, 2005 issued in European Patent Application No. 99 964 086.5, 3 pages.
European Decision to Refuse dated Dec. 15, 2005 issued in European Patent Application No. 99 964 086.5, 9 pages.
U.S. Office Action dated Feb. 14, 2007 issued in U.S. Appl. No. 10/890,909, 12 pages.
U.S. Office Action dated Apr. 11, 2007 issued in U.S. Appl. No. 10/931,890, 7 pages.
U.S. Office Action dated Sep. 13, 2007 issued in U.S. Appl. No. 10/890,909, 11 pages.
U.S. Office Action dated Sep. 13, 2007 issued in U.S. Appl. No. 10/931,890, 7 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Jun. 9, 2008 issued in U.S. Appl. No. 10/931,890, 10 pages.
U.S. Office Action dated Oct. 30, 2008 issued in U.S. Appl. No. 11/269,098, 12 pages.
U.S. Office Action dated Dec. 23, 2008 issued in U.S. Appl. No. 10/931,890, 9 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
Corrected Notice of Allowability dated Jul. 12, 2016, issued in U.S. Appl. No. 13/770,732, 6 pages.
Corrected Notice of Allowability dated Aug. 2, 2016, issued in U.S. Appl. No. 13/770,732, 6 pages.
International Search Report and Written Opinion dated Oct. 7, 2016, issued in PCT International Patent Application No. PCT/US2016/042272, 11 pages.
International Preliminary Report on Patentability dated Oct. 13, 2016, issued in PCT International Patent Application No. PCT/US2015/023590, 9 pages.
International Preliminary Report on Patentability dated Oct. 13, 2016, issued in PCT International Patent Application No. PCT/US2015/024256, 8 pages.
U.S. Office Action dated Oct. 23, 2014 issued in U.S. Appl. No. 13/477,997, 14 pages.
U.S. Office Action dated Dec. 2, 2014, issued in U.S. Appl. No. 13/770,732, 15 pages.
U.S. Office Action dated Jun. 10, 2015, issued in U.S. Appl. No. 13/770,732, 14 pages.

(56) References Cited

OTHER PUBLICATIONS

International Search Report and Written Opinion dated Jul. 2, 2015, issued in PCT Patent Application No. PCT/US2015/023590, 11 pages.
International Search Report and Written Opinion dated Jul. 10, 2015, issued in PCT Patent Application No. PCT/US2015/024256, 10 pages.
U.S. Office Action dated Aug. 10, 2015, issued in U.S. Appl. No. 14/231,392, 24 pages.
U.S. Office Action dated Jan. 15, 2016, issued in U.S. Appl. No. 13/770,732, 23 pages.
International Search Report and Written Opinion dated Feb. 26, 2016, issued in PCT Patent Application Serial No. PCT/US2015/066934, 11 pages.
International Search Report and Written Opinion dated Mar. 7, 2016, issued in PCT Patent Application Serial No. PCT/US2015/066778, 9 pages.
Final Office Action dated Mar. 22, 2016, issued in U.S. Appl. No. 14/231,392, 22 pages.
Notice of Allowance dated Jun. 15, 2016, issued in U.S. Appl. No. 13/770,732, 9 pages.
U.S. Office Action dated Nov. 30, 2016, issued in U.S. Appl. No. 14/231,392, 6 pages.
Office Action dated Nov. 30, 2018, issued in European Patent Application No. 15 772 648.0, 4 pages.
Office Action dated Dec. 25, 2018, issued in Japanese Patent Application No. 2017-503790, 12 pages. English language machine translation provided.
Examination Report dated Jan. 10, 2019, issued in Australian Patent Application No. 2015240953, 5 pages.
Office Action dated Feb. 6, 2019, issued in U.S. Appl. No. 15/301,498, 10 pages.
Intent to Grant dated Oct. 4, 2018, issued in European Patent Application No. 15871254.7, 7 pages.
Extended Search Report dated Jul. 4, 2018, issued in European Patent Application No. 15871254.7, 5 pages.
Partial Supplementary Search Report dated Aug. 2, 2018, issued in European Patent Application No. 15871198.6, 13 pages.
Office Action dated Aug. 29, 2018, issued in U.S. Appl. No. 15/267,537, 8 pages.
Notice of Allowance dated Sep. 12, 2018, issued in U.S. Appl. No. 15/210,268, 12 pages.
Extended Search Report dated Dec. 12, 2018, issued in European Patent Application No. 15871198.6, 15 pages.
Examination Report dated Jan. 16, 2019, issued in Australian Patent Application No. 2015240568, 5 pages.
Decision to Grant dated Feb. 5, 2019, issued in Japanese Patent Application No. 2017-503777, 4 pages.
Extended Search Report dated Mar. 1, 2019, issued in European Patent Application No. 16825172.6, 7 pages.
Office Action dated Oct. 17, 2018, issued in U.S. Appl. No. 15/301,498, 14 pages.
Notice of Allowance dated Oct. 30, 2018, issued in U.S. Appl. No. 15/210,268, 11 pages.
Office Action dated Dec. 10, 2018, issued in U.S. Appl. No. 14/975,638, 16 pages.
Office Action dated Jan. 7, 2019, issued in U.S. Appl. No. 14/974,851, 12 pages.
Notice of Allowance dated Jan. 10, 2019, issued in U.S. Appl. No. 15/267,537, 8 pages.

\* cited by examiner

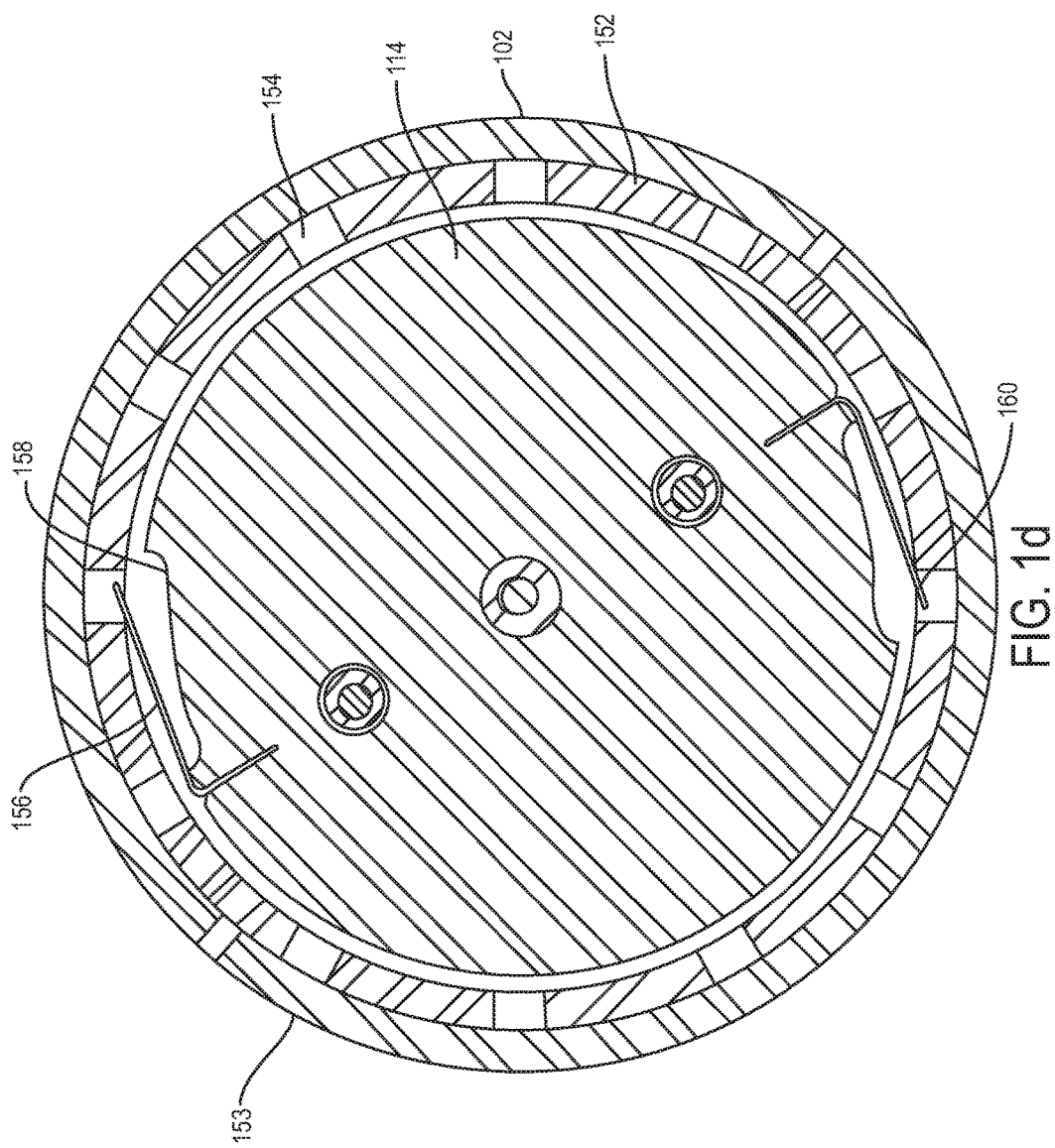

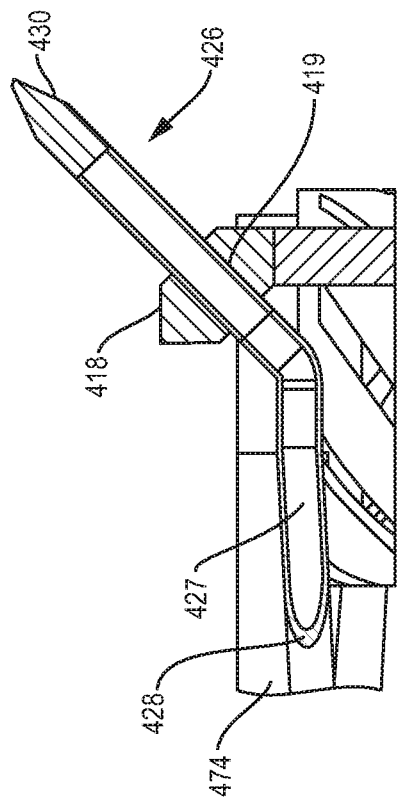
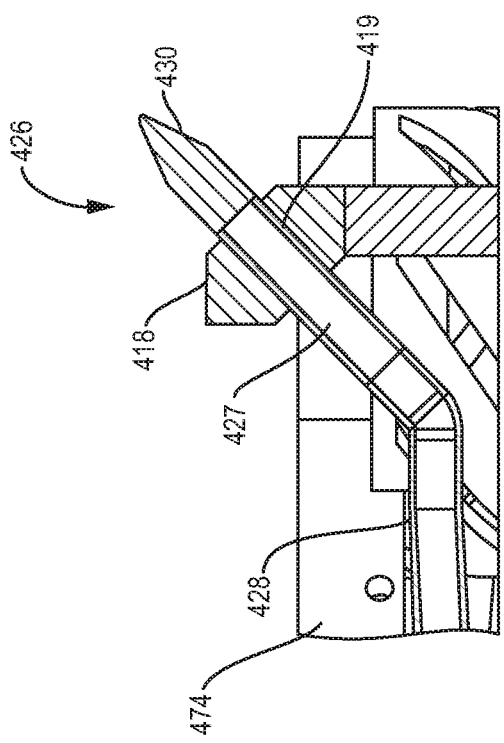
FIG. 4b
FIG. 4a

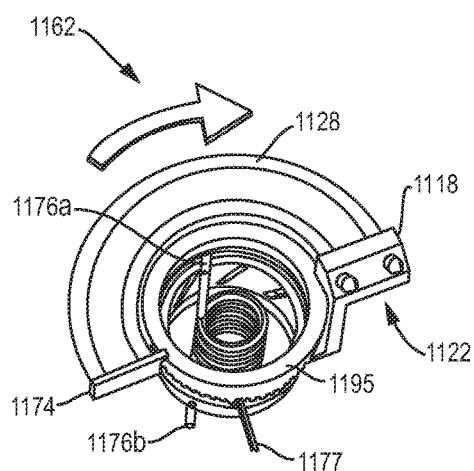 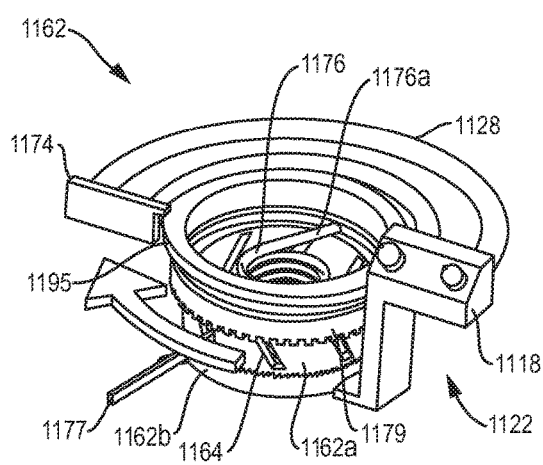
FIG. 15  FIG. 16
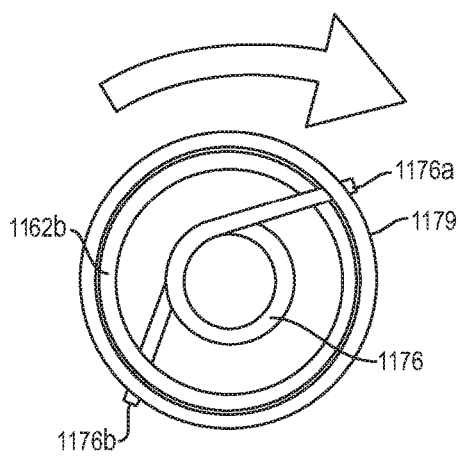 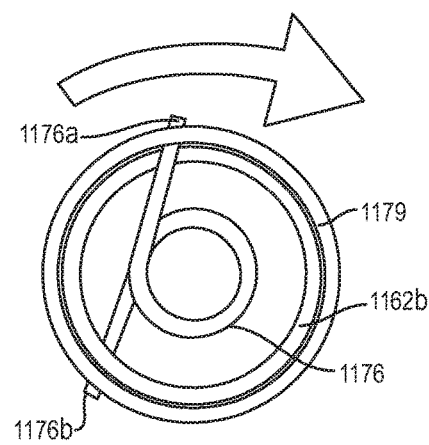
FIG. 17a  FIG. 17b

MEDICAL ACCESS PORT, SYSTEMS AND METHODS OF USE THEREOF

FIELD

The present disclosure relates generally to medical access ports and, in particular, to subcutaneous vascular access ports that may include one or more needles that penetrates the skin, wherein the needle(s) may extend or retract from the access port, and a position of the needle(s) may change in the access port to change the penetration location of the skin.

BACKGROUND

Hematology patients, oncology patients, hemodialysis patients and other patients may be subject to frequent infusion treatments delivering pharmaceuticals, blood, nutrients, contrasting agents and other compositions. Frequent "needle sticks" and the duration of infusion time may make receiving such treatments uncomfortable and creates scarring and added discomfort to the patient. Vascular access ports are medical devices that may be inserted beneath the skin (sub-cutaneous) and may reduce the discomfort associated with such treatments. A port may include an access point, such as a septum, into which a needle may be inserted. A port may also include a catheter, which may be inserted into a vein, such as a jugular vein, subclavian vein or superior vena cava. The septum may be formed of a self-healing silicone material that may be punctured multiple times with a relatively low loss in the integrity of the septum. However, a clinician needs to properly target the access port and a risk of infection may exist as a needle extending into the skin may drag bacteria from the skin into the port.

SUMMARY

Medical devices comprising implantable, subcutaneous, access ports, as well as actuators and systems, and methods of use thereof, are described for providing repeated therapy to a patient in need of such therapy. In certain embodiments, the access port, upon repeated use, may present an access needle at a new location/position of the access port each time the access port is utilized, so as to reduce and preferably minimize scarring injury to the tissue (skin) of the patient.

In certain embodiments, a medical device according to the present disclosure may include a subcutaneous access port having an access port body and at least one needle having a removable needle tip and a needle shaft defining a needle lumen; the at least one needle housed within the access port body, the at least one needle extendable and retractable relative to the access port body; and a needle shift mechanism operable such that the at least one needle is extendable from and retractable into the access port body at a plurality of positions of the access port body.

In certain embodiments, the needle shift mechanism may be operable such that the at least one needle is rotatable along an arcuate path about an axis of rotation. The arcuate path may be defined by a substantially constant radius from the axis of rotation, and may extend at least 90 degrees around the axis of rotation (e.g. at least 180 degrees around the axis of rotation, at least 270 degrees around the axis of rotation and 360 degrees around the axis of rotation)

In certain embodiments, the plurality of positions of the access port body may be arranged along the arcuate path, and the plurality of positions may be substantially equally spaced along the arcuate path.

In certain embodiments, the at least one needle may be rotatable along an arcuate path about an axis of rotation in only one direction.

In certain embodiments, the needle shift mechanism may comprise a ratcheting mechanism.

In certain embodiments, the access port body may comprise a cover; and the at least one needle may be extendable and retractable through the cover.

In certain embodiments, the access port body may comprise a septum; and the at least one needle may be extendable and retractable through the septum.

In certain embodiments, the access port body may comprise a plurality of needle openings; and the at least one needle may be extendable and retractable through each of the plurality of needle openings.

In certain embodiments, the plurality of needle openings may comprise a first needle opening and a second needle opening; and the needle shift mechanism may be operable to move the at least one needle from a first position in which the at least one needle is aligned with the first needle opening to extend and retract through the first needle opening to a second position in which the at least one needle is aligned with the second needle opening to extend and retract through the second needle opening.

In certain embodiments, the at least one needle having a removable tip and a needle shaft defining a needle lumen may further comprise a first needle having a removable first needle tip and a first needle shaft defining a first needle lumen, and a second needle having a removable second needle tip and a second needle shaft defining a second needle lumen; and the needle shift mechanism may be further operable such that the first needle is extendable from and retractable into the access port body at a plurality of first needle positions of the access port body, and the second needle is extendable from and retractable into the access port body at a plurality of second needle positions of the access port body.

In certain embodiments, the needle shift mechanism may be operable such that the first needle and the second needle are rotatable along an arcuate path about an axis of rotation.

In certain embodiments, the needle shift mechanism may be operable such that the first needle is rotatable along a first arcuate path about an axis of rotation, and the first needle is rotatable along a second arcuate path about the axis of rotation.

In certain embodiments, the needle shift mechanism may be operable with a button located on the access port.

In certain embodiments, the medical device may further comprise a needle elevator mechanism operable to extend the at least one needle from the access port body and retract the at least one needle into the access port body.

In certain embodiments, the access port body may comprise a cover having at least one opening; and the needle elevator mechanism may be operable to extend the at least one needle from the access port body through the at least one opening in the cover and retract the at least one needle into the access port body through the at least one opening in the cover.

In certain embodiments, the needle elevator mechanism may be operable to extend the at least one needle from the access port body and retract the at least one needle into the access port body by rotating the needle elevator mechanism about an axis of rotation.

In certain embodiments, the needle elevator mechanism may comprise an elevator member and a needle support member having the at least one needle supported thereon; and the elevator member may be threadably engaged with the needle support member and rotatable relative to the needle support member to extend the at least one needle from the access port body and retract the at least one needle into the access port body.

In certain embodiments, the elevator member may comprise a cylindrical member which is rotatable around the needle support member.

In certain embodiments, the elevator member may comprise a threaded rod which is rotatable in a threaded opening of the needle support member.

In certain embodiments, the needle elevator mechanism may comprise a ratcheting mechanism.

In certain embodiments, the needle elevator mechanism may comprise at least one magnet.

In certain embodiments, the at least one magnet may be magnetically engagable with an external actuator to extend the at least one needle from the access port body and retract the at least one needle into the access port body.

In certain embodiments, the at least one magnet is rotatable with the actuator to extend the at least one needle from the access port body and retract the at least one needle into the access port body.

In certain embodiments, the at least one magnet may be movable towards the actuator to extend the at least one needle from the access port body and movable away from the actuator to retract the at least one needle into the access port body.

In certain embodiments, the needle elevator mechanism may comprise a balloon arrangement.

In certain embodiments, the needle elevator mechanism may comprise a spring.

In certain embodiments, the needle elevator mechanism may be operable with a button located on the access port.

In certain embodiments, the medical device may further comprise at least one valve located within the access port to control a flow of fluid through the access port.

In certain embodiments, the at least one needle may comprise at least two needles; and the at least one valve may comprise a plurality of valves.

In certain embodiments, the medical device may further comprise a first channel bridging the at least two needles; and at least one of the plurality of valves arranged to open and close a flow of fluid across the first channel.

In certain embodiments, the medical device may further comprise at least two catheters; a second channel bridging the at least two catheters; and at least one of the plurality of valves arranged to open and close a flow of fluid across the second channel.

In certain embodiments, the access port may include a body, a cover with a plurality of openings, at least one needle with a tip and a shaft, the shaft defining a lumen, a needle elevator mechanism to operate the position of the at least one needle in at least a retracted position in which the at least one needle is disposed in the body and the needle tip below the cover and an extended position in which the at least one needle is protruding through at least a first one of the openings, and a needle shift mechanism to move the at least one needle from a first position in which the needle is aligned with a first one of the openings, to a second position in which the needle is aligned with a second one of the openings.

In certain embodiments, the access port may include a holder having the at least one needle disposed thereon and helical threads and the elevator mechanism may include helical threads positioned to engage with the thread of the holder. In some embodiments, the elevator mechanism may include a cylinder having thread in an interior surface, the needles being disposed inside the cylinder. In some embodiments, the elevator mechanism may include a rod having thread on an exterior surface, the needles being disposed beside the rod. In some other embodiments, the elevator mechanism may include at least one magnet. In some embodiments, the at least one magnet is a permanent magnet, or an electromagnet.

In certain embodiments, the needle shift mechanism may include a rotatable surface and at least one guide rod, the guide rod guiding the motion of the needle when the needle is being extended or retracted, and positioning the needle from the first position to the second position. In some embodiments, the needle shift mechanism may further include a slot and pin combination to position the needle at one of the at least first and second position. In some embodiments, the needle shift mechanism may further include a ratchet mechanism to position the needle at one of the at least first and second position.

In certain embodiments, the access port may also include a button that engages the needle shift mechanism to position the needle at one of the at least first to a second position. In certain embodiments, the needle shift mechanism can move the at least one needle from about six to about twelve positions. In some embodiments, at least one of the positions is a maintenance position which provides access to a replaceable part of the access port.

In certain embodiments, the access port may also include at least a valve to close flow of fluid through the at least one needle. In some embodiments, the access port may also include at least two needles and two valves, and a first channel bridging the two needles, wherein the valves close or open flow of fluid between the first channel and the at least two needles. In some embodiments, the access port may also include at least two vascular catheter inlets and a second channel bridging the two catheter inlets, wherein the valves close or open flow of fluid between the first channel and the at least two needles and between the second channel and the at least two vascular catheter inlets.

In a certain embodiment, an access port according to the present disclosure and the invention(s) disclosed herein may include a body defining at least two recesses for defining at least a first position and a second position, a cover with a plurality of openings, at least one needle including a tip and a shaft, the shaft defining a lumen, a cylinder having threads on an interior surface with the needles disposed inside the cylinder, a holder having the at least one needle disposed thereon and threads disposed to engage the threads of the cylinder, at least one magnet engaged with the cylinder to operate the position of the at least one needle in at least a retracted position in which the at least one needle is disposed in the body and the needle tip below the cover and an extended position in which the at least one needle is protruding through at least a first one of the openings; and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. In some embodiment, the base plate may further include at least a guide rod for engaging the at least one needle from the first position to the second.

In another embodiment, an access port according to the present disclosure and the invention(s) disclosed herein may include a body defining at least two recesses for defining at least a first position and a second position, a cover comprising a plurality of openings, at least one needle with a tip and a shaft, the shaft defining a lumen, a rod disposed along an axis of rotation of the access port and having threads on an exterior surface, a holder having the at least one needle disposed thereon and threads disposed to engage the threads of the rod, at least one magnet engaged with the rod to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. In some embodiments, the base plate may further include at least a guide rod for engaging the at least one needle from the first position to the second.

In some other embodiments, the access port may include a body, a cover including a plurality of openings at least one needle having a tip and a shaft, the shaft defining a lumen, a holder for carrying the at least one needle inside the port, a ratchet unit disposed along an axis of the access port and having a bottom portion having at least two teeth and processes and having a top portion defining at least two teeth and processes, the bottom teeth and processes capable of engaging the top teeth and processes defining at least a first position and a second position, a first button engaging the holder to operate the position of the at least one needle in at least a retracted position in which the at least one needle is disposed in the body and the needle tip below the cover and an extended position in which the at least one needle is protruding through at least a first one of the openings, and a second button engaging the ratchet unit to move the at least one needle from the first position in which the needle is aligned with a first one of the openings, to the second position in which the needle is aligned with a second one of the openings. In some embodiments, the top ratchet portion may further include at least two slots for engaging at least one pin, wherein when the pin is sliding along one of the slot, the at least one needle is raised or lowered, and when the pin is shifted from one of the slot to the other one, the at least one needle is shifted from the first position to the second position.

In yet other embodiments, the access port may include a body, a cover comprising a plurality of openings, at least two needles, each comprising a tip and a shaft, the shaft defining a lumen, a holder for carrying the needles inside the port, a ratchet unit disposed along an axis of the access port and having a bottom portion having at least two teeth and processes and having a top portion defining at least two teeth and processes, the bottom teeth and processes capable of engaging the top teeth and processes defining at least a first position and a second position, a magnet engaging the holder to position the needles from at least a retracted position in which the needles are disposed in the body and the needle tips below the cover to an extended position in which the needles are engaged through at least a first two of the openings, a coil spring to operate the holder to position the needles from at least an extended position in which the needles are engaged through at least two openings to a retracted position in which the needles are disposed in the body and the needle tips below the cover, at least two valves, a first channel bridging the two needles, wherein the valves close or open flow of fluid between the first channel and the at least two needles, at least two vascular catheter inlets, and a second channel bridging the two catheter inlets, wherein the valves close or open flow of fluid between the first channel and the at least two needles and between the second channel and the at least two vascular catheter inlets; and a button engaging the holder to move the at least one needle from the first position in which the needle is aligned with a first one of the openings, to the second position in which the needle is aligned with a second one of the openings.

In yet some embodiments, there is provided a system to access the vasculature of a patient. The system may include an access port and an actuator as described below. The access port may include a body defining at least two recesses for defining at least a first position and a second position, a cover comprising a plurality of openings, at least one needle comprising a tip and a shaft, the shaft defining a lumen, a cylinder having threads on an interior surface, the needles being disposed inside the cylinder, a holder having the at least one needle disposed thereon and threads disposed to engage the threads of the cylinder, at least one magnet engaged with the cylinder to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. The actuator may include a magnet, for positioning over the skin of a patient above the implanted access port. In some embodiments, the actuator magnet is an electromagnet.

In yet other embodiments, there is provided a system to access the vasculature of a patient. The system may include an access port and an actuator as described below. The access port may include a body defining at least two recesses for defining at least a first position and a second position, a cover comprising a plurality of openings, at least one needle comprising a tip and a shaft, the shaft defining a lumen, a rod disposed along an axis of rotation of the access port and having threads on an exterior surface, a holder having the at least one needle disposed thereon and threads disposed to engage the threads of the rod, at least one magnet engaged with the rod to operate the position of the at least one needle in at least a retracted position in which the at least one needle is disposed in the body and the needle tip below the cover and an extended position in which the at least one needle is protruding through at least a first one of the openings, and a base plate disposed in the body and having at least one flexible resilient prong engaging at least one of the at least two recesses of the body, the base plate engaging the at least one needle to move the at least one needle from the first position in which the needle is aligned with a first one of the openings, to the second position in which the needle is aligned with a second one of the openings. The actuator may include a magnet, for positioning over the skin of a patient above the implanted access port. In some embodiments, the actuator magnet is an electromagnet.

BRIEF DESCRIPTION OF THE DRAWINGS

The above-mentioned and other features of this disclosure, and the manner of attaining them, may become more apparent and better understood by reference to the following detailed description of embodiments described herein taken in conjunction with the accompanying drawings, wherein:

FIG. 1d illustrates a cross-sectional top view of the vascular access port of FIG. 1a, at the base plate level showing detail of the ratcheting mechanism;

FIG. 3b illustrates a side view of an example of the ratcheting mechanism as shown in FIG. 3a;

FIGS. 3c to 3e illustrate cross-sectional views of the ratcheting mechanism in various configurations according to the vascular access port as shown in FIG. 3a;

FIG. 4a illustrates a partial cross-sectional view of the needle arm of the vascular access port as shown in FIG. 3a, with the needles in the retracted position;

FIG. 4b illustrates a partial cross-sectional view of the needle arm of the vascular access port as shown in FIG. 3a, with the needles in the extended position;

FIG. 5a illustrates a perspective view of a vascular access port as shown in FIG. 3a;

FIG. 5c illustrates a perspective view of a vascular access port as shown in FIG. 5a;

FIGS. 8b to 8d illustrate side views of the ratcheting mechanism various configurations as shown in FIG. 8a;

FIG. 15 illustrates a perspective view of the ratcheting mechanism as shown in FIG. 12, with the needles in the retracted position;

FIG. 16 illustrates a perspective view of the ratcheting mechanism as shown in FIG. 12, with the needles in the retracted position;

FIGS. 17a and 17b illustrate top views of the various configurations of a torsion spring used in the ratcheting mechanism as shown in FIG. 12;

DETAILED DESCRIPTION

Figure 1A:
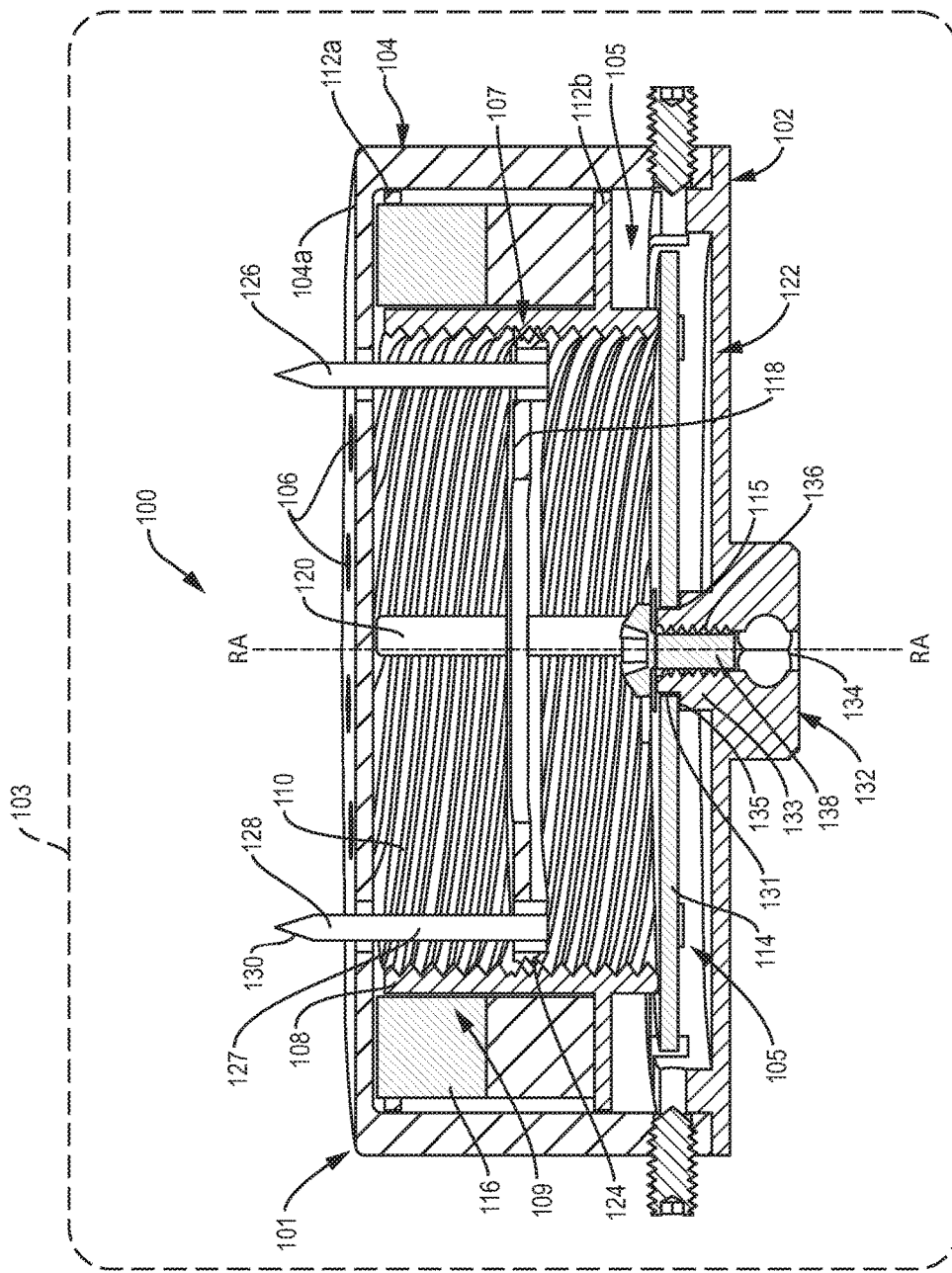
FIG. 1a illustrates a cross-sectional view of an example of a vascular access port contemplated herein, with the needles in the partially extended position.

It is to be understood that this disclosure is not limited in its application to the details of construction and the arrangement of components set forth in the following description or illustrated in the drawings. The embodiments herein are capable of other embodiments and of being practiced or of being carried out in various ways.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Spatial references such as "above," "below," "top," "bottom," "horizontal," "vertical," "right," "left," and the like are meant to be understood in relation to the orientation of the device and parts thereof as illustrated in the figure being described, and are interchangeable upon spatial reorientation of the device.

Embodiments herein may refer to motion of moving parts as clockwise or counter-clockwise. Such embodiments should not be regarded as limiting of the invention as mirror-image embodiments can be adapted to perform the same operation or function in a reverse sense of motion, counterclockwise or clockwise as appropriate.

The present disclosure relates generally to medical access ports and, in particular, to sub-cutaneous vascular access ports that may be connected to a blood vessel, body cavity or organ of a patient via one or more internal (indwelling) catheters. The access ports may include at least one extendable/retractable needle. For certain medical applications, such as hemodialysis, two needles may be required for the exit of blood from the patient and return of the clean blood to the patient. The embodiments of the access ports described herein focusing on ports having two needles are equally applicable to ports having one needle, or more than two needles. The needles may puncture through the skin of a patient, providing access to the port. A catheter or other device may be affixed to the needles protruding from the port and through the skin of the patient to deliver a composition to the patient. The needles may also puncture a vial stopper to deliver a composition stored in the vial.

In general, the access ports may provide one or more extendable/retractable needles operated by a needle elevator mechanism. In addition, the access ports may also provide multiple positions for the one or more needles to extend/retract, so that the one or more needles will extend/retract at a new position for each use. The one or more needles may be shifted, particularly by being rotated, from a first position to the next position by a needle shift mechanism inside the port. The needle elevator mechanism may be operated with an external actuator, or with an internal actuator within the port. Similarly, the shift mechanism may be operated with an external actuator, or with an internal actuator within the port.

Examples of suitable external actuators may include permanent magnets or electromagnets. Examples of suitable internal actuators may include buttons, levers, switches and the like.

Figure 1B:
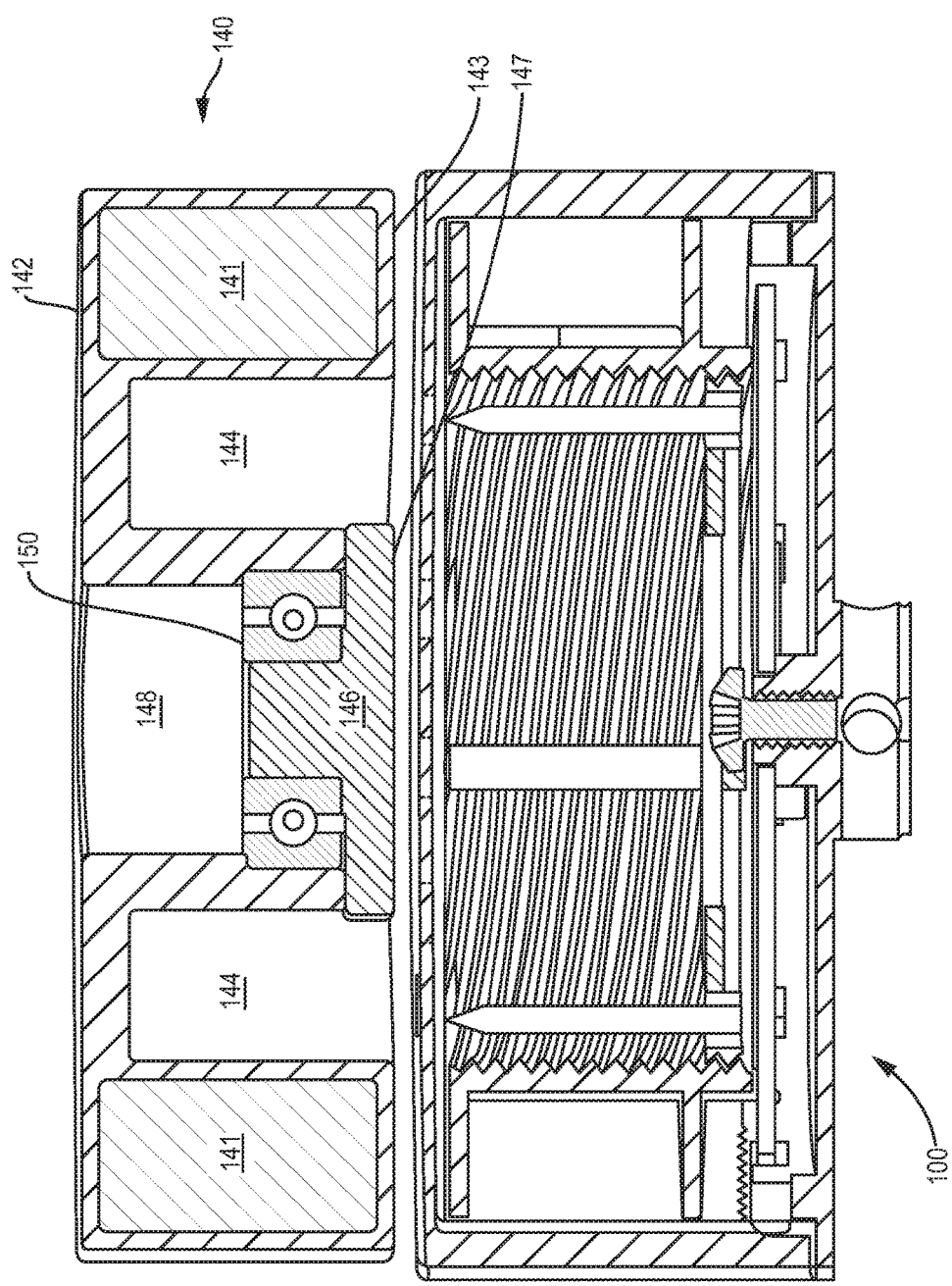
FIG. 1b illustrates a cross-sectional view of the vascular access port of FIG. 1a paired with an actuator, with the needles in the retracted position.

FIGS. 1a and 1b illustrate an example of an access port 100 which may include at least one needle 126, and more particularly two needles 126. In FIG. 1a, the two needles 126 are shown in an at least partially extended (exposed) position, and in FIG. 1b, the two needles are shown in a fully retracted (concealed) position. In such regards, it may be understood that the needles 126 travel axially (parallel) along a center/rotational axis RA of the access port 100 as described herein.

The needles 126 may include a hollow shaft 128 for connecting a fluid path with an internal catheter accessing a blood vessel (not shown), and a closed, pointed, removable tip 130 which allows access to a lumen 127 of the needles 126 for the passage of fluids (e.g. medication, blood). The needles 126 may be made of medical grade steel, or of a ferromagnetic material, or may include a ferromagnetic material at the tip 130.

FIG. 1a illustrates the access port 100 may further include a body 101 comprising a base 102, generally having a shape of a circular plate, supporting an overlying cylindrical cover 104, which cooperate to form an inner cavity 105. Base 102 includes a hub 132 that serves as the connection area to which catheters or other devices used may be attached. Details of such connections are well known and not illustrated here.

The cover 104 may include on the top surface/wall 104a a series of predefined openings 106 to allow the passage of needles 126 through the top wall 104a of the cover 104 to retract into and extend out of the body 101 of the access port 100. As shown, for example, in FIG. 7a, the openings 106 may be arranged in a circular (arcuate) ring pattern and, in certain embodiments, in the form of two concentric (arcuate) rings as an outer ring and an inner ring.

In order to prevent access of body fluids and/or ingrowth of tissue into the openings 106 in the access port 100, the access port 100 may be contained in a housing 103 (shown in phantom), which may be made of a "self-healing" material, such as silicone. When extended, the needles 126 may pierce through the self-healing material. Thereafter, when the needles 126 are retracted, the openings 106 created in the self-healing material may sufficiently close (i.e. self-close) so that the access port 100 remains impervious to body fluids and ingrowth of body tissue. Alternatively, the cover 104, and more particularly the top wall 104a of the cover 104, may be made of a self-healing material, and the needles 126 may pierce through the top wall 104a of the cover 104, which may sufficiently close (i.e. self-close) after the needles 126 are retracted to inhibit ingress of to body fluids and ingrowth of body tissue.

The cavity 105 of the access port 100 may contain a needle elevator mechanism 107, which may comprise a cylindrical (elevator) member 109, which may rests and rotate on a circular floor 114. As explained herein, the floor 114 of the needle elevator mechanism 107 may also operate as part of a needle shift mechanism 122. As shown, the base 102 supports floor 114 and provides the structural foundation for the needle elevator mechanism 107 and the needle shift mechanism 122, as well as forms part of the needle shift mechanism 122.

To secure the floor 114 and the base 102 to one another, the floor 114 may include a center circular opening 115 having a diameter to receive a spindle 131 formed by a threaded, shouldered, screw boss 133 of the hub 132 of the base 102. Once on the spindle 131, floor 114 may rest on the shoulder 135 of the boss 133 and be secured to the boss 133 by a threaded screw fastener 138 (and a washer/seal 134) which couples with the threads 136 of boss 133, and retains the floor 114 perpendicular to the screw boss 133. As explained in greater detail below, the floor 114, and more particularly the needle elevator mechanism 107 and the needle shift mechanism 122, may rotate about an axis of rotation RA of the access port 100, here provided by the spindle 131, where the elevator mechanism moves the needles 126 axially along the axis of rotation RA and the needle shift mechanism 122 moves the needles circumferentially (radially) around the axis of rotation RA.

Cylindrical (elevator) member 109 of the needle elevator mechanism 107 comprises a cylinder 108 which may include internal threads 110, as well as outer peripheral flanges 112, provided by upper flange 112a and lower flange 112b. The flanges 112a, 112b may be used to hold at least one permanent magnet 116 in a fixed position there between.

The needle elevator mechanism 107 may further comprise a needle support member 118. The access port needles 126 may be secured to (fastened) and supported within the interior of the cylinder 108 by the needle support member 118, which generally has a shape of an annular plate. One or more elongated guide post members 120 maintain a preselected circumferential (radial) position of the needles 126 in the access port 100 during an operation of the needle elevator mechanism 107 that elevates and retracts the needles 126, in and out of the body 101 of the access port 100. The needle support member 118 may have external threads 124 on the periphery that engage the internal threads 110 of the cylinder 108.

FIG. 1*b* further illustrates the access port 100 paired with a separate actuator 140. The actuator 140 may include at least one magnet 141 (e.g. permanent magnet or an electromagnet) in body 142, which may be used as a handle, as well as a circular chamber 144 that receives the needles 126 in the extended configuration. The actuator 140 may include bearings 150 disposed in a central bore 148 between the body 142 and a center rotational support 146, which ease rotation of the body 142 relative to the rotational support 146. As shown, the front (skin contact) face 147 of the rotational support 146 is offset (stepped) and projects outwardly relative to the front surface 143 of the body 142 to provide a gap/spacing to keep the main body 142 from overly contacting the surface of the skin or sterile covering for the skin of the patient and easing rotation of the body 142 of the actuator 140.

In operation, the access port 100 may be positioned under the skin of a host, particularly a patient, such as a patient particularly in need of repeated vascular access. Medical personnel (e.g. physician, clinician) may then position the actuator 140 onto the skin above (overlying) the implanted access port 100, at which time the magnets 141 placed within body 142 may operate the needle elevator mechanism 107 inside the access port 100.

When the magnets 141 of the actuator 140 are electromagnets, and the magnets 116 of the access port 100 are permanent magnets, the actuator magnets 141 magnetically engage with the magnets 116 within the port 100 and induce rotation of the cylindrical (elevator) member 109. More particularly, when an electric current of a first polarity is provided to electromagnet 141, electromagnet 141 may emit an electro-magnetic field arranged with a first polarity which attracts the permanent magnet 116 of the access port 100. Thereafter, rotation of the body 142 of the actuator 140 about rotational support 146 will correspondingly result in rotation of the cylindrical (elevator) member 109 of the access port 100 about the rotational axis RA.

The rotation of the cylindrical (elevator) member 109 causes the sliding rotation of the external threads 124 of the needle support member 118 along the internal threads 110 of the cylinder 108, moving the needles 126 upward or downward along the axis of rotation RA depending on the direction of the rotation of the cylindrical (elevator) member 109. For example, counter-clockwise rotation of the body 142 of the actuator 140 and cylindrical (elevator) member 109 of the access port 100 may elevate the needle support member 118 and needles 126, while clockwise rotation of the body 142 of the actuator 140 and cylindrical (elevator) member 109 of the access port 100 may retract the needle support member 118 and needles 126.

FIG. 1*a* illustrates the access port 100 with the needles 126 in the partially extended position with the tips 130 of the needles 126 slightly protruding from the cover 104 of the access port 100. FIG. 1*b* illustrates the access port 100 with the needles 126 in the retracted position before actuation of the access port 100. Among other benefits, the mechanical engagement provided by threads 110 and 124 allows the needles 126 to be arranged in a fully extended (axial) position, a fully retracted (axial) position, or be partially extended/retracted at any (axial) position there between.

The access port 100 may also include a needle shift mechanism 122 that, upon full retraction of the needles 126 into the vascular port 100, shifts/rotates a circumferential (radial) position of the needles 126 inside the cylinder 108 of the cylindrical (elevator) member 109 around the axis of rotation RA provided by the spindle 131 such that, upon subsequent use and reactivation of the access port 100, the needles 126 will protrude from the port at a new, different location through the cover 104. One example of such needle shift mechanism 122 is described below and illustrated in FIGS. 1*c* and 1*d*.

Figure 1C:
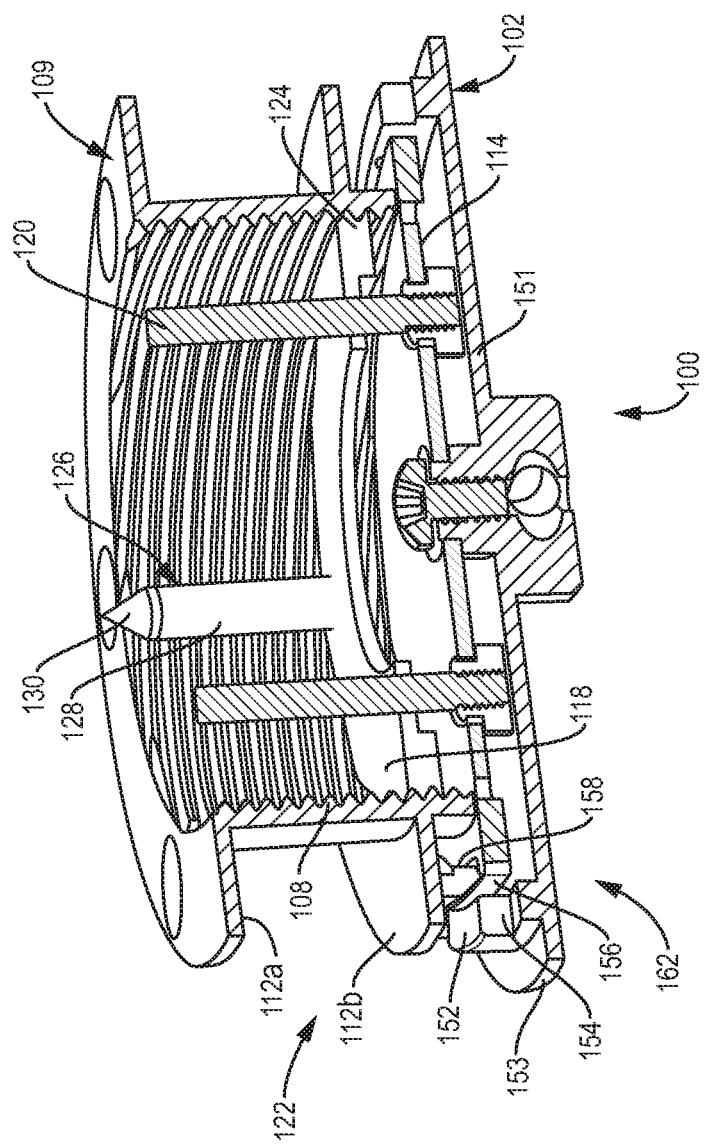
FIG. 1c illustrates a cross-sectional view of the internal parts of the vascular access port of FIG. 1a, without the cover and the magnets.

Referring to FIGS. 1*c* and 1*d*, the access port 100 may include a needle shift mechanism 122, and more particularly a ratcheting mechanism 162, that may move the position of the needles 126 within the access port 100 at the end of each use, so that, on the next use of the access port 100, the needles 126 will pierce the skin at a new, different location and minimize the patient discomfort due to excessive scarring which may occur when the needles 126 exit the skin repeatedly at the same location.

In FIG. 1*c*, the base 102 may include a circular base portion 151 (which extends substantially transverse to the axis of rotation RA of the needle elevator mechanism 107 and the needle shift mechanism 122), as well as a raised circular rim 152 which extends substantially transverse to the circular base portion 151 (i.e. substantially parallel to the axis of rotation RA). As shown, circular rim 152 is located proximally adjacent the peripheral edge 153 of the circular base portion 151 of the base 102 and surrounds the floor 114.

The circular rim 152 may include a plurality of slots 154 which, as explained in greater detail herein, predetermine the various circumferential (radial) positions that the needles 126 may occupy in the access port 100. In certain embodiments, there may be from two to twenty slots 154, and more particularly six to twelve slots 154, that may be uniformly spaced apart at regularly spaced intervals (i.e. the same) around the circular rim 152. The number of slots 154 may depend on the intended repeated use of the access port 100, with more slots 154 corresponding to greater use thereof. In the displayed embodiment, the circular rim 152 includes twelve slots 154 which afford six positions for two needles 126, or twelve positions for one needle 126, to pierce the skin of a patient at a new, different location.

The ratcheting mechanism 162 further includes at least one flexible and resilient (deformable) engagement member 156, such as a linear spring (which may be deformed towards recess 158), connected to or integral (i.e. one monolithic piece) with the floor 114, which may engage with any one of the slots 154. As shown, the engagement members 156 are arranged to engage a slot 154 at an engagement angle such that, the floor 114 may be rotated in one direction but not the other direction. More particularly, when the floor 114 is rotated in one direction, but not in the opposite direction, the terminal end (extremity) 160 of the engagement members 156 abuts (contacts) a vertical sidewall of the slot 154 in which it resides.

Due to the angle of engagement and the configuration of the engagement members 156, the engagement members 156 prevent the floor 114 from rotating in one direction (e.g. the clockwise direction) when the needles 126 are being raised (due to the terminal end 160 contacting the vertical sidewall of the slot 154). Conversely, the engagement members 156 allow the floor 114 to rotate in the opposite direction (e.g. the counter-clockwise direction) by deforming inward against the circular rim 152 and out of the slot 154 once the needles 126 have been fully retracted and the needle support member 118 frictionally engages with the floor 114. At this point, the floor 114 rotates counterclockwise from a first circumferential (radial) position to the next available circumferential (radial) position afforded by the slots 154. Alternately, the direction of the threads 110, 124 of cylinder 108 and needle support member 118, respectively, and the design of the ratcheting mechanism shown in FIG. 1d could be reversed to make the ratcheting mechanism rotate in the opposite direction.

As set forth above, the needle shift mechanism 122, and more particularly the ratcheting mechanism 162, may operate by friction of the needle support member 118 onto the floor 114, or by the engagement of a pin/notch combination (not shown) positioned between the needle support member 118 and the floor 114 so as to engage one another once the needle support member 118 has reached is lowermost position in the access port 100 against the floor 114.

With the foregoing needle shift mechanism 122, and more particularly ratcheting mechanism 162 such as one detailed in FIG. 1d, rotation of the floor 114 may be understood to stop at one of the defined positions for subsequent extension and retraction. The ratcheting mechanism 162 may provide an auditory signal (e.g. a "click") when it reaches one of the defined circumferential (radial) positions. The design allows medical personnel to further rotate the needles 126 to other further circumferential (radial) positions if it is so desired to avoid a sensitive location for the patient.

Figure 2A:
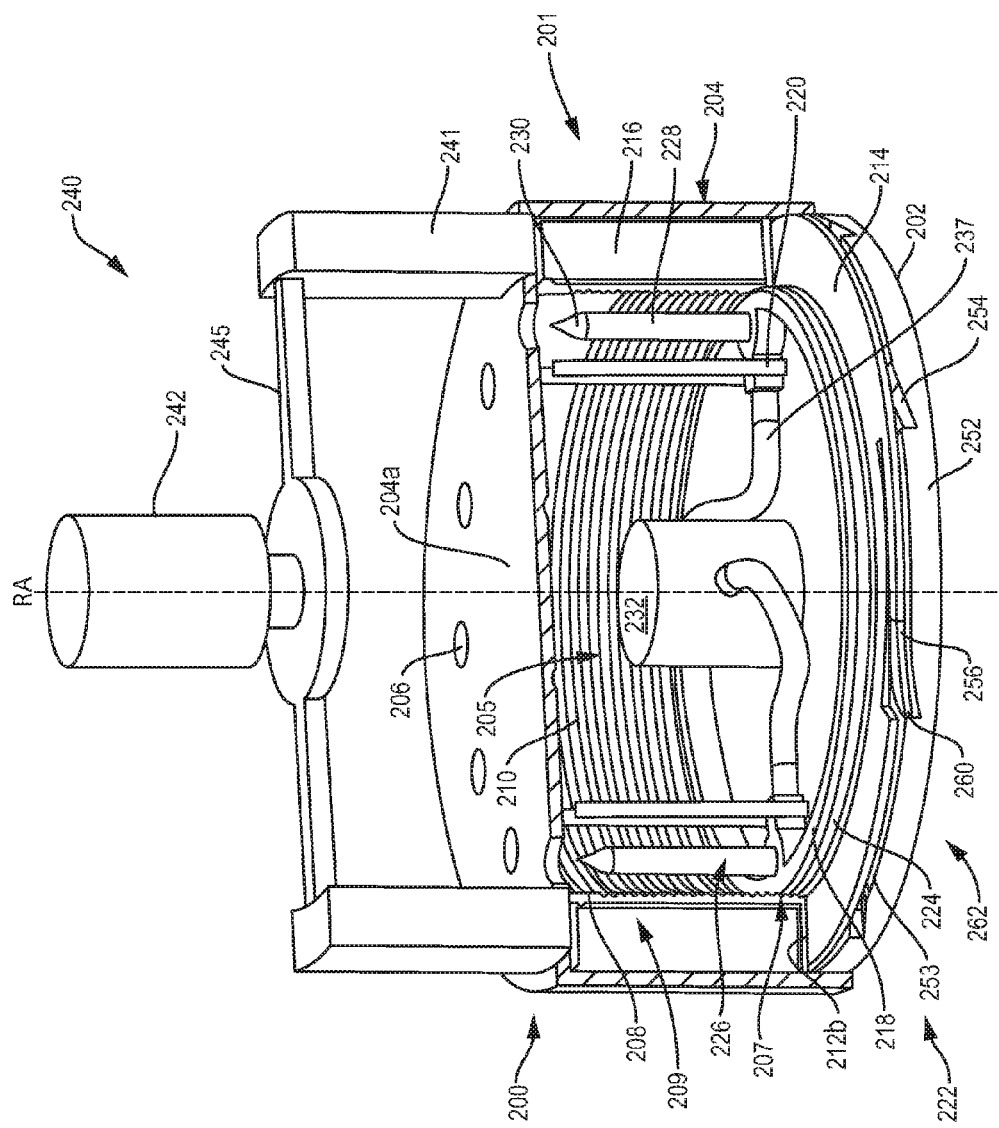
FIG. 2a illustrates a cross-sectional view of an example of a vascular access port contemplated herein paired with an actuator, showing an example of a ratcheting mechanism.

FIGS. 2a to 2d illustrate another example of an access port 200 with an alternate needle shift mechanism 222, and more particularly a ratcheting mechanism 262. As with the first embodiment, FIG. 2a illustrates the access port 200 may include a base 202 supporting an overlying cover 204, which cooperate to form an inner cavity 205.

Also as with the first embodiment, the cover 204 may include on the top surface/wall 204a a series of predefined openings 206 to allow the passage of needles 226 through the top wall 204a of cover 204 to retract into and extend out of the body 201 of the access port 200. The needles 226 may include a hollow shaft 228 for connecting a fluid path with an internal catheter accessing a blood vessel (not shown), and a closed, pointed, removable tip 230 which allows access to a lumen 227 of the needles 226 for the passage of fluids (e.g. medication, blood). The needles 226 may be made of medical grade steel, or of a ferromagnetic material, or may include a ferromagnetic material at the tip 230.

As with the prior embodiment, in order to prevent access of body fluids and/or ingrowth of tissue into the openings 206 in the access port 200, the access port 200 may be contained in a housing 203 (not shown, similar to housing 103), which may be made of a "self-healing" material, such as silicone. When extended, the needles 226 may pierce through the self-healing material. Thereafter, when the needles 226 are retracted, the openings 206 created in the self-healing material may sufficiently close (i.e. self-close) so that the access port 200 remains impervious to body fluids and ingrowth of body tissue. Alternatively, the cover 204, and more particularly the top wall 204a of the cover 204, may be made of a self-healing material, and the needles 226 may pierce through the top wall 204a of the cover 204, which may sufficiently close (i.e. self-close) after the needles 226 are retracted to inhibit ingress of to body fluids and ingrowth of body tissue.

The cavity 205 of the access port 200 may contain a needle elevator mechanism 207, which may comprise a cylindrical (elevator) member 209, which rests and rotates on circular floor 214. As explained herein, the floor 214 of the needle elevator mechanism 207 may also operate as part of the needle shift mechanism 222. As shown, the base 202 supports floor 214 and provides the structural foundation for the needle elevator mechanism 207 and the needle shift mechanism 222, as well as forms part of the needle shift mechanism 222. As explained in greater detail below, the floor 214, and more particularly the needle elevator mechanism 207 and the needle shift mechanism 222, may rotate about an axis of rotation RA of the access port 200.

Cylindrical (elevator) member 209 of the needle elevator mechanism 207 comprises a hollow cylinder 208 which includes internal threads 210, as well as outer peripheral flanges 212 provided by upper flange 212a and lower flange 212b. The flange 212a, 212b may be used to support and hold at least one permanent magnet 216 in a fixed position there between.

The needle elevator mechanism 207 further comprises a needle support member 218. The access port needles 226 are secured to (fastened) and supported within the interior of the cylinder 208 by the needle support member 218. One or more elongated guide post members 220 maintain a preselected circumferential (radial) position of the needles 226 in the access port 200 during an operation of the needle elevator mechanism 207 that elevates and retracts the needles 226, in and out of the body 201 of the access port 200. The needle support member 218 may have external threads 224 on the periphery that engage the internal threads 210 of the cylinder 208. The needles 226 may each include a shaft 228 connected to a flexible linking tube 237 connected a central (post) hub 232. The central hub 232 may include channels that connect to catheters that access the blood vessel (not shown).

In operation, the access port 200 may be positioned under the skin of a patient (such as a patient particularly in need of repeated vascular access) and operated with an actuator 240 overlying the skin. The actuator 240 may comprise a center hub 242, which may provide a cylindrical body/handle which is located on and extends along the axis of rotation RA. The actuator 240 further comprises two laterally extending arms 245 which extend transverse to the axis of rotation RA on opposing sides of the hub 242. Each arm 245 may support and hold at least one permanent magnet 241 fixed to the arm 245.

Medical personnel (e.g. physician, clinician) may position the actuator 240 onto the skin above (overlying) the access port 200, at which time the magnets 241 may operate the needle elevator mechanism 207 inside the access port 200.

As set forth with the first embodiment, the actuator magnets 241 magnetically engage with the magnets 216 within the access port 200 and induce rotation of the cylindrical (elevator) member 209. The rotation of the cylindrical (elevator) member 209 causes the sliding rotation of the external threads 224 of the needle support member 218 along the internal threads 210 of the cylinder 208, moving the needles 226 upward or downward along the axis of rotation RA depending on the direction of the rotation of the cylindrical (elevator) member 209.

Figure 2B:
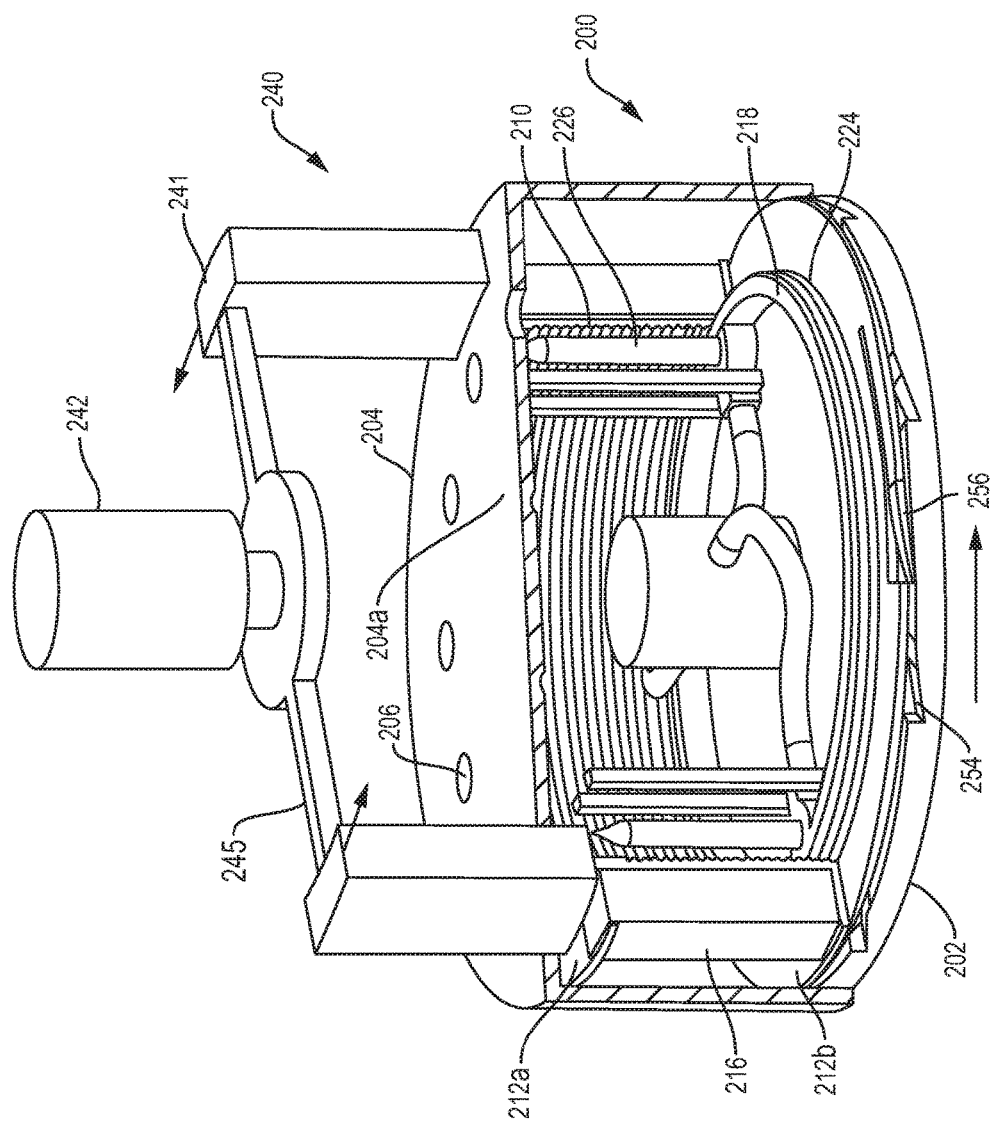
FIGS. 2b to 2d illustrate cross-sectional views of the ratcheting mechanism of FIG. 2a, in various configurations.
Figure 2C:
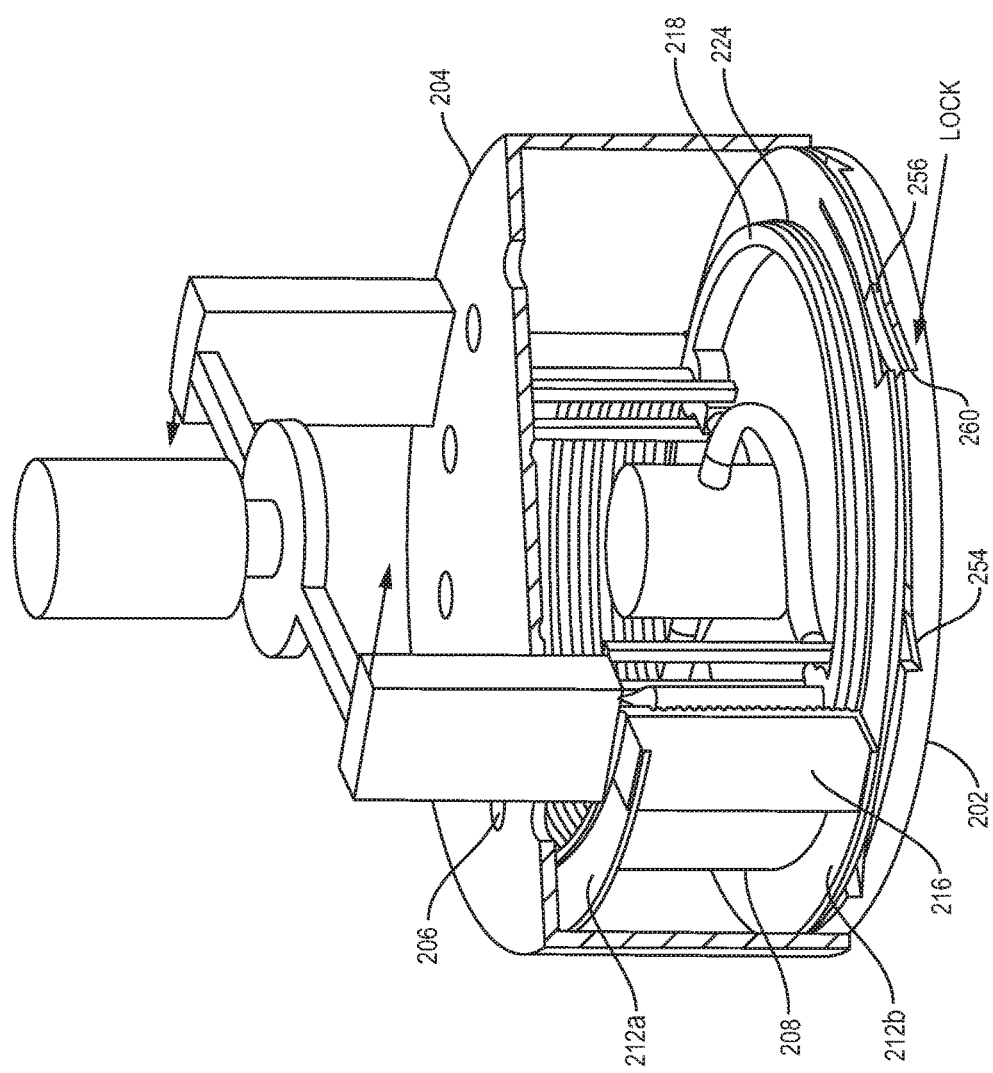
Figure 2D:
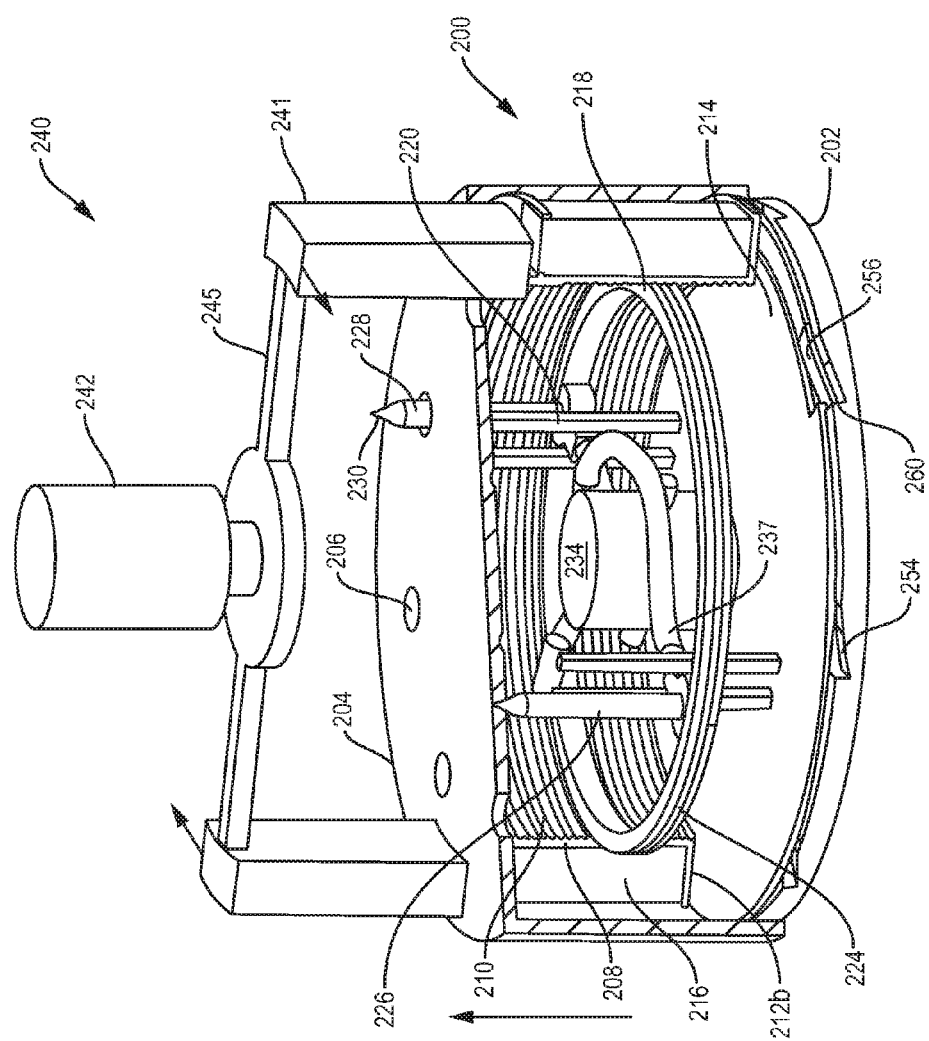

FIGS. 2a-d illustrate the sequence of motions generated by the needle shift mechanism 222 inside the access port 200 that moves (rotates) the needles from a first circumferential (radial) position (FIG. 2a) to a second circumferential (radial) position (FIG. 2c). FIG. 2a illustrates the access port 200 with the needles 226 in the retracted position at a first circumferential (radial) position of the access port 200 after use. FIG. 2b illustrates the access port 200 with the needles 226 in transit and being rotated to a second circumferential (radial) position. FIG. 2c illustrates the access port 200 with the needles 226 at the second circumferential (radial) position.

As shown in FIGS. 2a-2d, the needle shift mechanism 222 is operable such that the needles 226 are rotatable along an arcuate path about an axis of rotation RA. In the illustrated embodiment, the arcuate path is defined by a substantially constant radius (while access port 200 may be designed to rely upon a constant radius, the radius may vary slightly due to operational tolerances of the needle shirt mechanism) from the axis of rotation RA. The arcuate path my extent at least 90 degrees around the axis of rotation RA, and particularly at least 180 degrees around the axis of rotation RA, and more particularly at least 270 degrees around the axis of rotation RA, and even more particularly 360 degrees around the axis of rotation RA. The plurality of predetermined circumferential (radial) positions of the access port body 201 are arranged along the arcuate path, and more particularly the plurality of positions are substantially equally spaced along the arcuate path.

Moreover, the needle shift mechanism 222 is operable to move the needles 226 from a first position in which the needles 226 are aligned with the first needle opening to extend and retract through the first needle opening to a second position in which the needles 225 are aligned with the second needle opening to extend and retract through the second needle opening.

In FIG. 2a, the base 202 may include at the peripheral edge 253 including plurality of slots 254 which predetermine the various circumferential (radial) positions that the needles 226 may occupy in the access port 200. In certain embodiments, there may be from two to twenty slots 254, and more particularly six to twelve slots 254, that may be uniformly (equally) spaced apart at regularly spaced intervals (i.e. the same) around the peripheral edge 252. The number of slots 254 may depend on the intended repeated use of the access port 200, with more slots 254 corresponding to greater use thereof. In the displayed embodiment, the peripheral edge 253 includes twelve slots 254 which afford six circumferential (radial) positions for two needles 226, or twelve positions for one needle 126, to pierce the skin of a patient at a new, different location.

The ratcheting mechanism further includes at least one flexible and resilient (deformable) engagement member 256, which is shown as a bent portion integral (i.e. one monolithic piece) with the floor 214, which may engage with any one of the slots 254. As shown, the engagement members 256 are arranged to engage a slot 254 at an engagement angle such that the terminal end (extremity) 260 of the engagement members 256 abuts (contacts) a vertical sidewall of the slot 254 in which it resides.

Due to the angle of engagement and the configuration of the engagement members 256, the engagement members 256 prevent the floor 214 from rotating in one direction (e.g. the clockwise direction) when the needles 226 are being raised (due to the terminal end 260 contacting the vertical sidewall of the slot 254). Conversely, the engagement members 256 allow the floor 214 to rotate in the opposite direction (e.g. the counter-clockwise direction) by deforming upwardly once the needles 226 have been fully retracted and the needle support member 218 frictionally engages with the floor 214. At this point, the floor 214 rotates counter-clockwise from a first circumferential (radial) position to the next available circumferential (radial) position afforded by the slots 254. Alternatively, the design of the ratcheting mechanism could be reversed to rotate in the opposite direction.

As set forth above, the needle shift mechanism 222, and more particularly the ratcheting mechanism 262 may operate by friction of the needle support member 218 onto the floor 214, or by the engagement of a pin/notch combination (not shown) positioned between the needle support member 218 and the floor 214 so as to engage one another once the needle support member 224 has reached is lower most position in the access port 200 against the floor 214.

With the foregoing needle shift mechanism 222, and more particularly ratcheting mechanism 262 such as one detailed in FIG. 2a, rotation of the floor 214 may be understood to stop at one of the defined positions for subsequent extension and retraction. The ratcheting mechanism 262 may provide an auditory signal (e.g. a "click") when it reaches one of the defined circumferential (radial) positions. The design allows the medical personnel (e.g. physician, clinician) to further rotate the needles 226 to other further circumferential (radial) positions if it is so desired, such as to avoid a sensitive location for the patient.

Figure 3A:
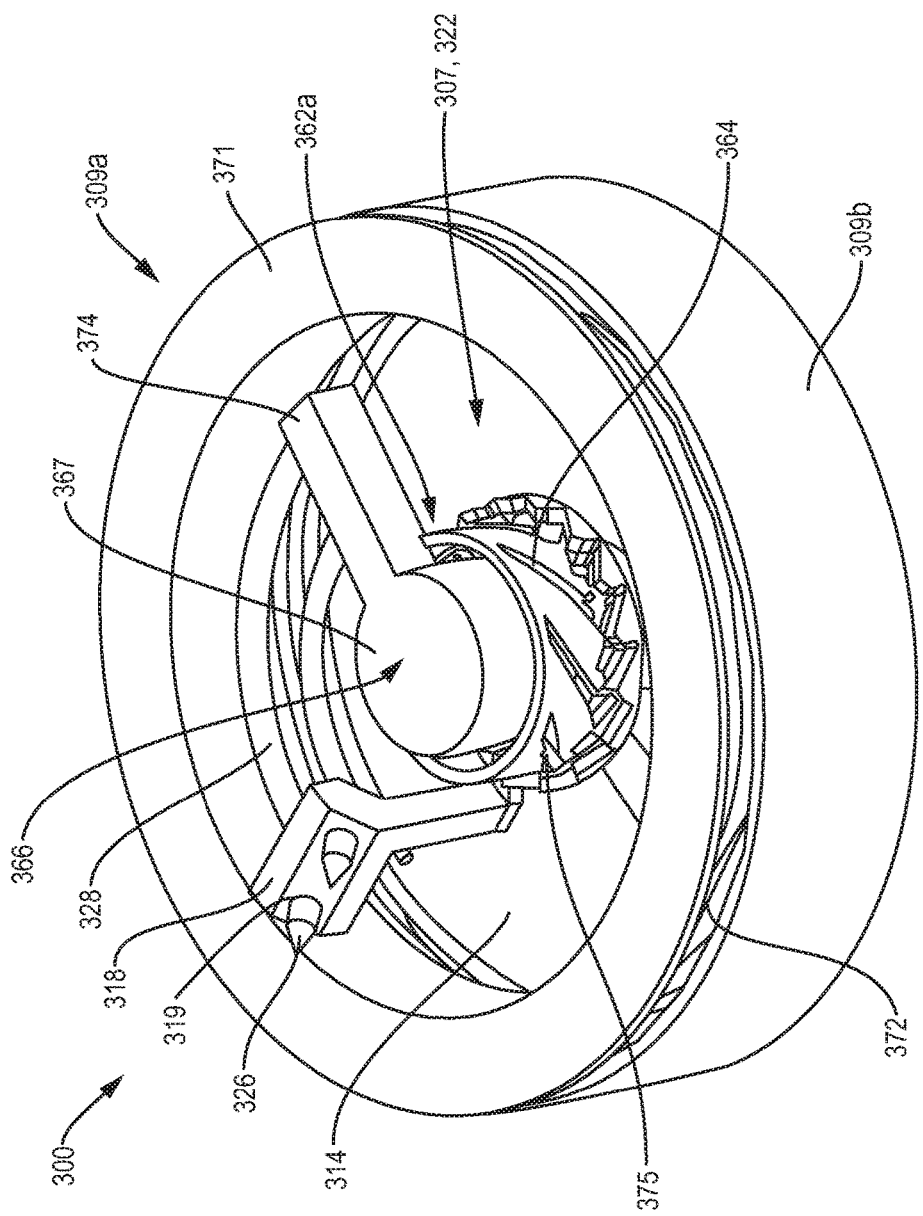
FIG. 3a illustrates a perspective view of an alternate example of a vascular access port contemplated herein, with the needles in the retracted position.
Figure 3B:
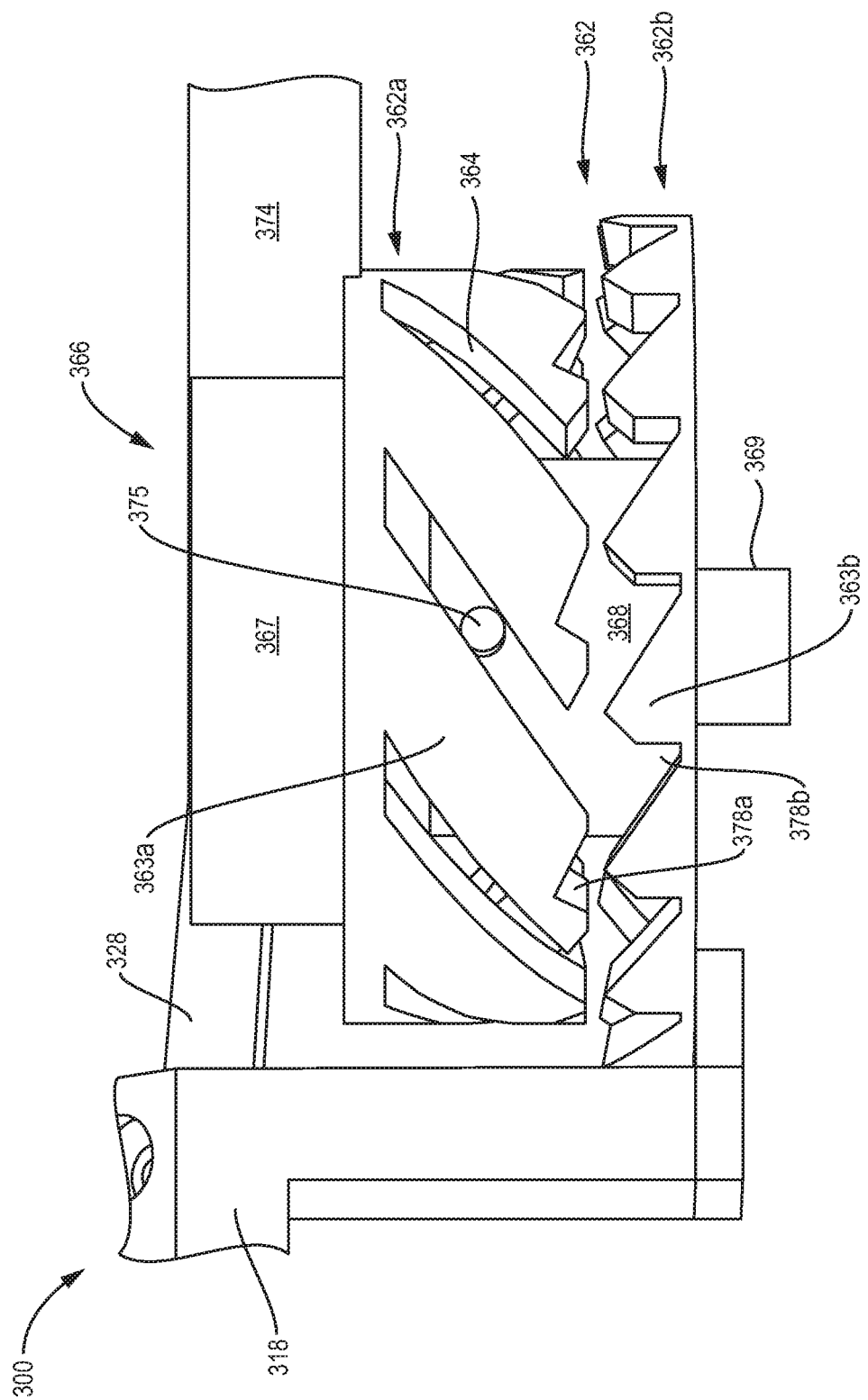

FIGS. 3a and 3b illustrate another example of an access port 300. Similar to the previous embodiments, the needle elevator mechanism 307 and the needle shift mechanism 322 may both rotate around an axis of rotation RA to extend/retract the needles 326 axially, as well as to change a circumferential (radial) position of the needles 326. In this embodiment, the cover 304 has been removed to expose the needle elevator mechanism 307 and needle shift mechanism 322. More particularly, the needle elevator mechanism 307 and the needle shift mechanism 322 may both operate via a circular ratcheting mechanism 362 disposed in the center of the access port 300, which may comprise an upper (top) annular cylindrical ratchet portion 362a disposed above a lower (bottom) annular cylindrical ratchet portion 362b which engage and disengage from each other to extend/retract the needles 326 and change the circumferential (radial) position of the needles 326.

As best shown by FIG. 3b, inside the access port 300, the needles 326 may be supported by a needle (arm) support member 318 that is connected (fixed) to the lower ratchet portion 362b of a ratcheting mechanism 362. More particularly, the needle support member 318 is disposed circumferentially alongside ratchet teeth 363b of lower ratchet portion 362b. The upper ratchet portion 362a includes ratchet teeth 363a which are separated by elongated openings (which may also be referred to as cam slits or slots) 364, which are oblique to the axis of rotation RA.

Access port 300 further includes an internal actuator 366, as opposed to the separate actuator used for the prior embodiments. Internal actuator 366 comprises a cylindrical push button 367 disposed over a hub 368 which moves (strokes) circumferentially on central spindle (shaft) 369 located within the confines of circular ratcheting mechanism 362.

Button 367 may be depressed by pushing down on cover 304 (which overlies button 367), at which time hub 368 (which is disposed beneath button 367) may move downward, with hub 368 moving downward along spindle 369. Furthermore, cover 304 may apply a compression force to the circular flange 371 of inner cylindrical member 309a and move inner cylindrical member 309a downward into outer cylindrical member 309b. The depression is biased by a coil spring 372 disposed beneath cylindrical flange 371 between inner cylindrical member 309a and outer cylindrical member 309b, which returns the cover 304/push button 367 to its pre-depressed position after the depression force is removed. As will become more apparent with further reading of the disclosure, the coil spring 372 serves to separate upper (top) ratchet portion 362a and lower (bottom) annular ratchet portion 362b until the button 367 is depressed.

The upper ratchet portion 362a further includes a laterally projecting arm 374 that holds the needle shafts 328. The arm 374 fits into a slot of the upper edge of the upper ratchet portion 362a, so as to move it rotationally along with the needles 326. The arm 374 contains fluid flow channels (not shown) connected and in fluid communication with the lumens 327 of needle shafts 328 at one end, and to the (vascular) catheters (not shown) at the other end. More particularly, the fluid flow channels direct flow for each needle 326 to a catheter supplying each needle 326 at the bottom of the access port 300.

As shown, hub 368 may include at least one cam pin 375 which protrudes outwardly (transverse) to the axis of rotation RA, and which may be located in elongated cam slot opening 364. When the button 367 is depressed, particularly by the medical personnel, such may operates the needle elevator mechanism 307 and the needle shift mechanism 322, particularly via ratcheting mechanism 362. More particularly, as button 367 begins to travel downward, hub 368 and cam pin 375 may simultaneously travel downward, particularly without rotating. Due to the cam slots 364 being arranged oblique to the axis of rotation RA, as cam pin 375 travels downward, it forces upper ratchet portion 362a to rotate counter-clockwise as the cam pin 375 travels downward in cam slot 364. Due to counter-clockwise rotation of upper ratchet portion 362, the adjoining laterally projecting arm 374 also rotates counter-clockwise, at which time needle shafts 328 of needles 326, extend through needle extension and retraction through-holes 319 formed in needle support member 318. As shown, the needle extension and retraction through-holes 319 is also oblique to the axis of rotation RA. As such, when needle shafts 328 of needles 326, which may comprise flexible semi-rigid tubing, are forced through through-holes 319 by the counter-clockwise rotation of upper ratchet portion 362, the needles extend and rise through the through-holes 319 to operate the needle elevator mechanism 307.

As button 367 continues to travel downward, upper (top) annular cylindrical ratchet portion 362a and lower (bottom) annular cylindrical ratchet portion 362b are brought into engagement with the upper ratchet teeth 363a and lower ratchet teeth 363b contacting to operate the needle shift mechanism 322. More particularly, the notches 378a of the upper ratchet teeth 363a of upper ratchet portion 362a engage with the notches 378b of the lower ratchet teeth 363b of lower ratchet portion 362b forcing the lower ratchet portion 362b to rotate clockwise one notch at a time for each depression of the button 367, rotating with it the needle support member 318 clockwise and thus positioning the needles 326 at a new circumferential (radial) position to operate the needle shift mechanism 322.

Figure 3E:
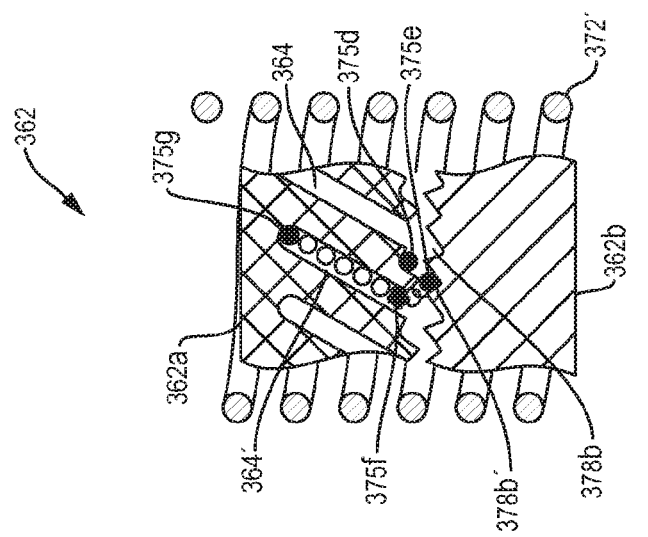
Figure 3D:
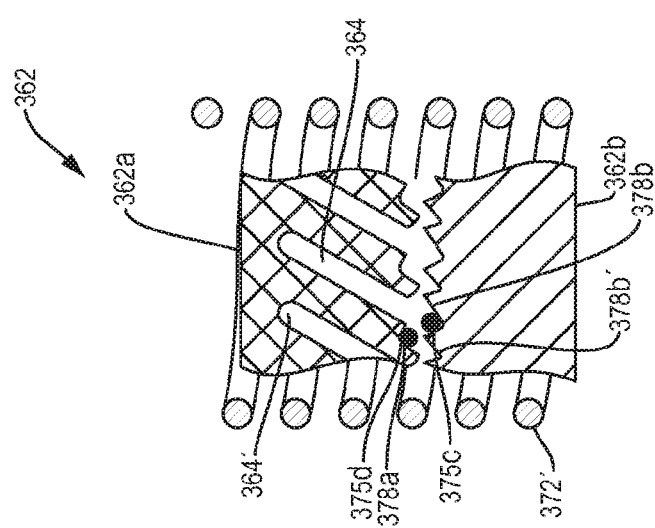
Figure 3C:
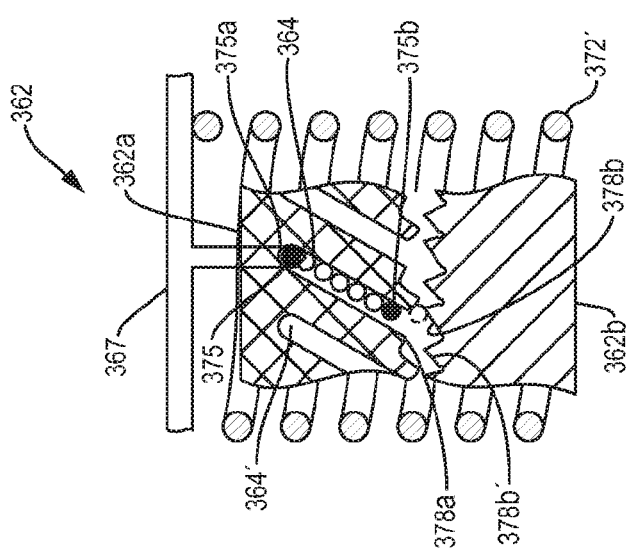

FIGS. 3c to 3e illustrate various stages of the operation of the ratcheting mechanism 362 of access port 300 shown in FIG. 3a. In the first stage, shown in FIG. 3c, the upper ratchet portion 362a and lower ratchet portion 362b of the ratcheting mechanism 362 are disposed inside a coil spring 372' similar to coil spring 372. For simplicity, button 367 is shown directly connected to cam pin 375 engaged in cam slot 364 in the upper ratchet portion 362a. When the button 367 is depressed the first time, cam pin 375 travels down cam slot 364 from position 375a to 375b until it reaches the bottom of notch 378b of the bottom lower ratchet portion 362b where it stops downward progress at position 375c. During this time, as set forth above, the upper ratchet portion 362a rotates counter-clockwise to operate the needle elevator mechanism 307 and, when teeth 363a, 363b engage, the lower ratchet portion 362b rotates clockwise to operate the needle shift mechanism 322.

As such, upon release of the button 367, the cam pin 375 now shifts (transfers) to notch 378a of the upper ratchet portion 362a at position 375d where it lodges and maintains the button 367 in a depressed configuration as shown in FIG. 3d, and needles 326 in an extended (raised) position. Referring to FIG. 3e, when the button is depressed a second time, the cam pin 375 shifts (transfers) to position 375e engaging notch 378b' of the lower ratchet portion 362b disposed clockwise of notch 378a of upper ratchet portion 362a. Upon release of the button 367 again, the cam pin 375 shifts (transfers) into adjacent cam slot 364' at position 375f of the upper ratchet portion 362a, disposed clockwise to cam slot 364 to settle at and travels to the top of cam slot 364' at position 375g, during which time the upper ratchet portion rotates clockwise and needles 326 return to their retracted (lowered) position. As the can pin 375 travels from position 375a to 375g, the ratcheting mechanism 362 rotates the needles clockwise into a new position inside the access port 300.

FIGS. 4a and 4b illustrate the retracted and extended position of the needles 426 in relation to the needle support member 418 with a portion of the needle shaft 428 in cross-section to show the lumen 427 of the needle 426. As the needle arm 474 rotates counter-clockwise, the proximal portion of the needle shaft 428 is pushed upward through through-holes 419 formed in needle support member 418, lifting the tips 430 of the needles 426.

Figure 5A:
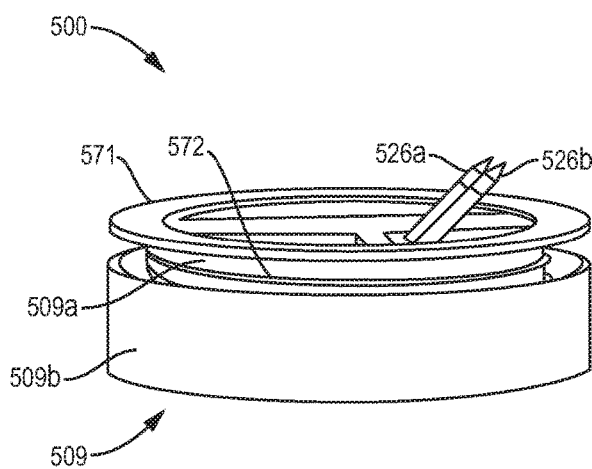

FIG. 5a illustrates a perspective view of the interior of an access port 500 similar to the port shown in FIG. 3a. As set forth with the prior embodiment, a cylindrical member 509 may comprise an inner cylindrical member 509a and an outer cylindrical member 509b having a coil spring 572 located therebetween.

Figure 5B:
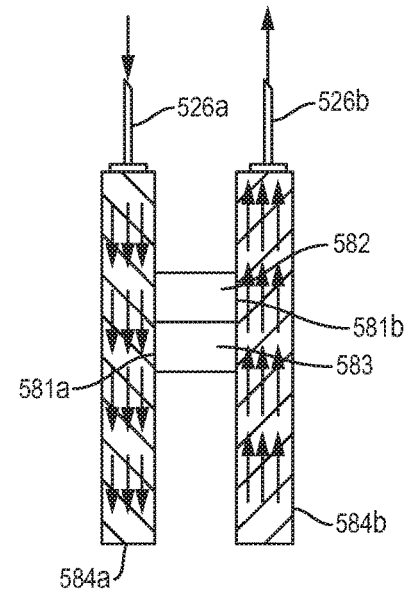
FIG. 5b illustrates a side view of the operation of the needles of a vascular access port as shown in FIG. 5a, in a blood flow mode.

As shown in FIG. 5a, coil spring 572 is decompressed and the circular flange 571 of inner cylindrical member 509a is flush with the top rim of a smaller annular (cylindrical) frame 580. The inner cylindrical member 509a is propped in an upward position with coil spring 572. In this configuration, the needles 526a and 526b operate in blood flow mode, as shown in FIG. 5b, where valve 581a of needle 526a is open and in a vertical position preventing access to top bridge 582 and bottom bridge 583. The same is observed for needle 526b, where valve 581b of needle 526b is open and in a vertical position preventing access to top bridge 582 and bottom bridge 583. The flow of blood can thus enter needle 526a and exit needle 526b as when the access port 500 is used for hemodialysis of a patient with kidney failure.

Figure 5C:
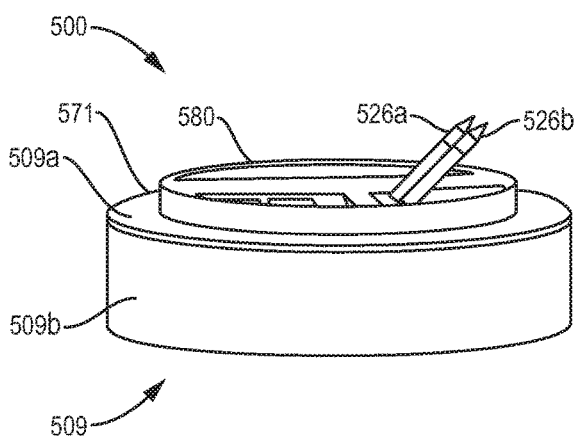
Figure 5D:
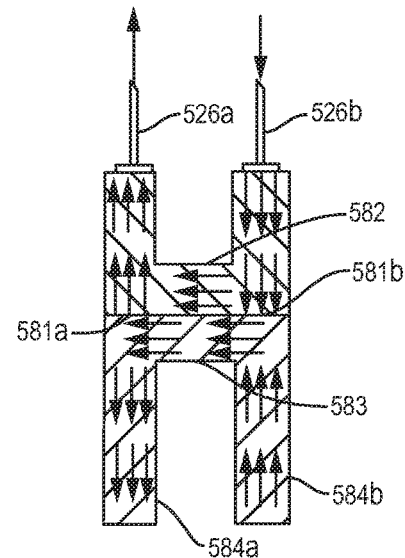
FIG. 5d illustrates a side view of the operation of the needles of a vascular access port as shown in FIG. 5a, in a needle-cleaning mode.

FIG. 5c illustrates a configuration in which coil spring 572 is compressed and the circular flange 571 of the inner cylindrical member 509a is depressed and flush to the rim of the outer cylindrical member 509b. In this configuration, the needles 526a and 526b operate in cleaning mode, as shown in FIG. 5d, where valve 581a of needle 526a and valve 581b of needle 526b are closed and prevent the blood flow in needles 526a and 526b creating a lower loop for the blood flow from catheter 584b to catheter 584a in bottom bridge 583, and allow access to top bridge 582 from the needles 526b and 526a for a cleansing solution, which may be used to prevent the formation of blood clots in the needles 526a and 526b.

Figure 6:
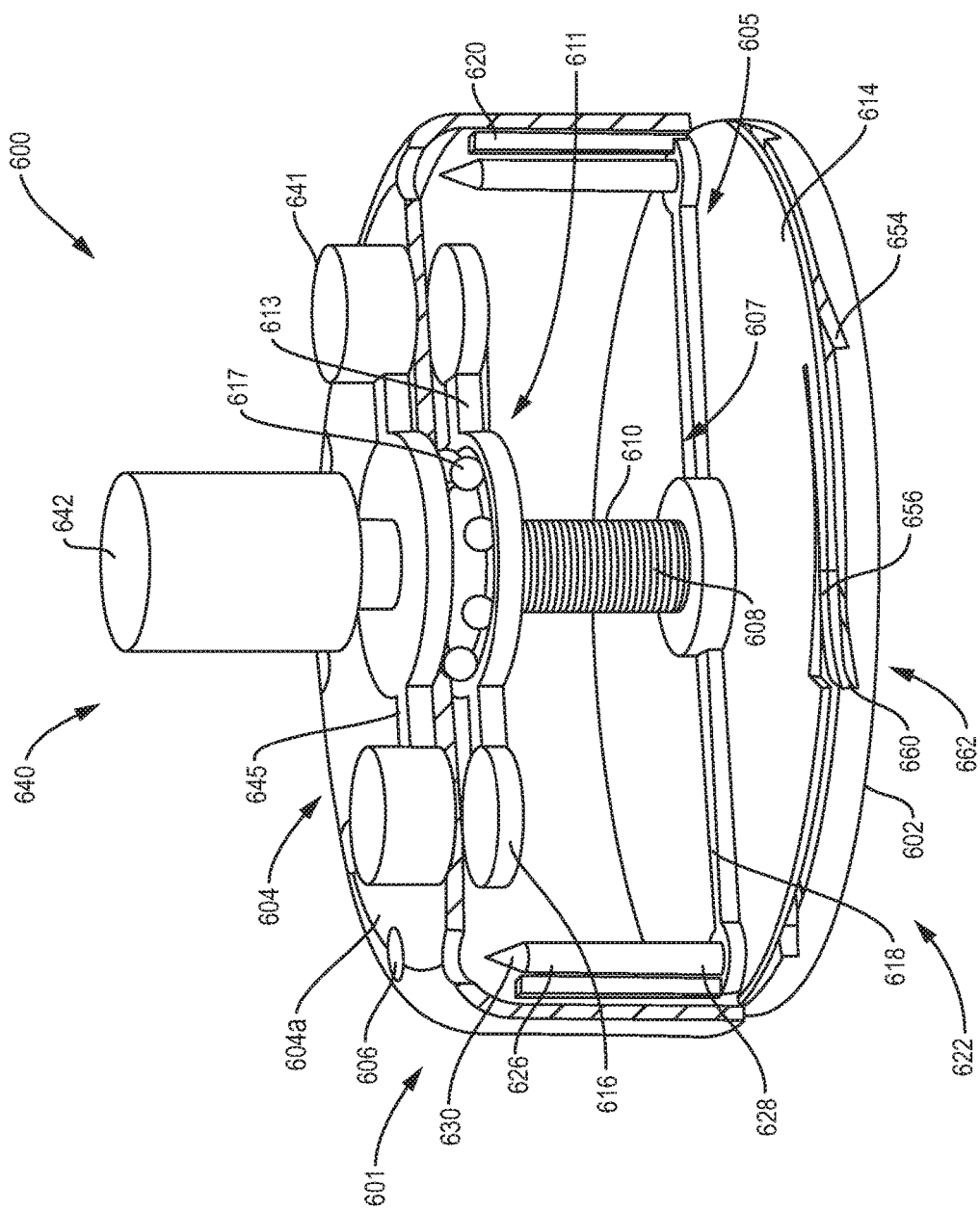
FIG. 6 illustrates a cross-sectional view of an example of a vascular access port contemplated herein paired with an actuator, with the needles in the retracted position.

FIG. 6 illustrates another example of an access port 600 also with a needle shift mechanism 622, and more particularly a ratcheting mechanism 662. As with prior embodiments, the access port 600 may include a base 602 supporting an overlying cover 604, which cooperate to form an inner cavity 605.

As with prior embodiments, the cover 604 may include on the top surface/wall 604a a series of predefined openings 606 to allow the passage of needles 626 through the top wall 604a of cover 604 to retract into and extend out of the body 601 of the access port 600. The needles 626 may include a hollow shaft 628 for connecting a fluid path with an internal catheter accessing a blood vessel (not shown), and a closed, pointed, removable tip 630 which allows access to a lumen of the needles 626 for the passage of fluids (e.g. medication, blood). The needles 626 may be made of medical grade steel, or of a ferromagnetic material, or may include a ferromagnetic material at the tip 630.

As with prior embodiments, in order to prevent access of body fluids and/or ingrowth of tissue into the openings 606 in the access port 600, the access port 600 may be contained in a housing 603 (not shown, similar to housing 103), which may be made of a "self-healing" material, such as silicone. When extended, the needles 626 may pierce through the self-healing material. Thereafter, when the needles 626 are retracted, the openings 606 created in the self-healing material may sufficiently close (i.e. self-close) so that the access port 600 remains impervious to body fluids and ingrowth of body tissue. Alternatively, the cover 604, and more particularly the top wall 604a of the cover 604, may be made of a self-healing material, and the needles 626 may pierce through the top wall 604a of the cover 604.

The cavity 605 of the access port 600 contains a needle elevator mechanism 607, which rests and rotates on circular floor 614. As explained herein, the floor 614 of the needle elevator mechanism 607 may also operate as part of the needle shift mechanism 622. As shown, the base 602 supports floor 614 and provides the structural foundation for the needle elevator mechanism 607 and the needle shift mechanism 622, as well as forms part of the needle shift mechanism 622. As explained in greater detail below, the floor 614, and more particularly the needle elevator mechanism 607 and the needle shift mechanism 622, may rotate about an axis of rotation RA of the access port 600.

Needle elevator mechanism 607 comprises a center (elevator) hub/member 611 which provides a center rotational support. Center (elevator) hub/member 611 includes a threaded cylinder (rod) 608, which includes external threads 610 and rotates about an axis of rotation RA of the access port 600. Needle elevator mechanism 607 further comprises two laterally extending arms 613 which extend transverse to the axis of rotation RA on opposing sides of the center (elevator) hub/member 611. Each arm 613 may support and hold at least one permanent magnet 616 fixed to the arm 611. The center (elevator) hub/member 611 may include a ball bearing system 617 to facilitate the rotation of the magnets 616 in the access port 600 while extending (raising) and retracting (lowering) the needles 626.

The needle elevator mechanism 607 further comprises a needle support member 618. The access port needles 626 are secured to (fastened) and supported within the cavity 605 by the needle support member 618. One or more elongated guide member 620 maintain a pre-selected circumferential (radial) position of the needles 626 in the access port 600 during an operation of the needle elevator mechanism 607 that elevates and retracts the needles 626, in and out of the body 601 of the access port 600. The needle support member 618 may have internal threads 624 at the center that engage the external threads 610 of the central threaded rod 608. The needles 626 may each include a shaft 628 to connect, through a fluid path, with a catheter accessing the blood vessel (not shown).

In operation, the access port 600 may be positioned under the skin of a patient (such as a patient particularly in need of repeated vascular access) and operated with an actuator 640 overlying the skin. The actuator 640 may comprise a center hub 642, which may provide a cylindrical body/handle which is located on and extends along the axis of rotation RA. The actuator 640 further comprises two laterally extending arms 645 which extend transverse to the axis of rotation RA on opposing sides of the hub 642. Each arm 645 may support and hold at least one permanent magnet 641 fixed to the arm 245.

Medical personnel (e.g. physician, clinician) may position the actuator 640 onto the skin above the access port 600, at which time the magnets 641 may operate the needle elevator mechanism 607 inside the access port 600.

The actuator magnets 641 magnetically engage with the magnets 616 within the access port 600 and induce rotation of the central rod 608. The rotation of the central rod 608 causes the sliding rotation of the internal threads 624 of the needle support member 618 along the external treads 610 of the central rod 608, and with the help of the elongated guide members 620, moving the needles 626 upward or downward along the access of rotation RA depending on the direction of the rotation of the central rod 608.

The access port 600 may also include a needle shift mechanism 622 that, upon full retraction of the needles 626 into the access port 600, shifts the circumferential (radial) position of the needles 626 inside the access port 600 such that upon a subsequent activation of the access port 600, the needles 626 will protrude from the vascular access port 600 at a new circumferential (radial) position.

As shown before in FIG. 6, such needle shift mechanism 622 may particularly comprise a ratcheting mechanism 662 that moves the position of the needles 626 within the access port 600 at the end of each use, so that on the next use of the access port 600, the needles 626 will pierce the skin at a new location. The base 602 may include at the peripheral edge 653 a defined plurality of slots 654 which predetermine the various circumferential (radial) positions that the needles 626 may occupy in the access port 600. In certain embodiments, there may be from two to twenty slots 654, and more particularly six to twelve, slots 654, that may be uniformly spaced apart at regularly spaced intervals (i.e. the same) around the peripheral edge 652. The number of slots 654 may depend on the intended repeated use of the access port 600, with more slots 654 corresponding to greater use thereof. In the displayed embodiment, the peripheral edge 653 includes twelve slots 654 which afford six circumferential (radial) positions for two needles 626, or twelve positions for one needle 626, to pierce the skin of a patient at a new, different location.

The ratcheting mechanism 662 further includes at least one flexible and resilient (deformable) engagement member 656, which is shown as a bent portion integral (i.e. one monolithic piece) with the floor 614, which may engage with any one of the slots 654. As shown, the engagement members 656 are arranged to engage a slot 654 at an engagement angle such that the terminal end (extremity) 660 of the engagement members 656 abut (contacts) a vertical sidewall of the slot 654 in which it resides.

Due to the angle of engagement and the configuration of the engagement members 656, the engagement members 656 prevent the floor 614 from rotating in one direction (e.g. the clockwise direction) when the needles 626 are being raised (due to the terminal end 660 contacting the vertical sidewall of the slot 654). Conversely, the engagement members 656 allow the floor 614 to rotate in the opposite direction (e.g. the counter-clockwise direction) by deforming upwardly once the needles 626 have been fully retracted and the needle support member 618 frictionally engages with the floor 614. At this point, the floor 614 rotates counter-clockwise from a first circumferential (radial) position to the next available circumferential (radial) position afforded by the slots 654. Alternatively, the design of the ratcheting mechanism 662 could be reversed to rotate in the opposite direction.

The ratcheting mechanism 662 may operate by friction of the needle support member 618 onto the floor 614, or by the engagement of a pin/notch combination (not shown) positioned between the needle support member 618 and the floor 614 so as to engage one another once the needle support member 624 has reached is lowermost position in the access port 600. Due to a ratcheting mechanism 662 such as one detailed in FIG. 6, rotation of the floor 614 will tend to stop at one of the pre-defined positions for later needle extraction.

Figure 7A:
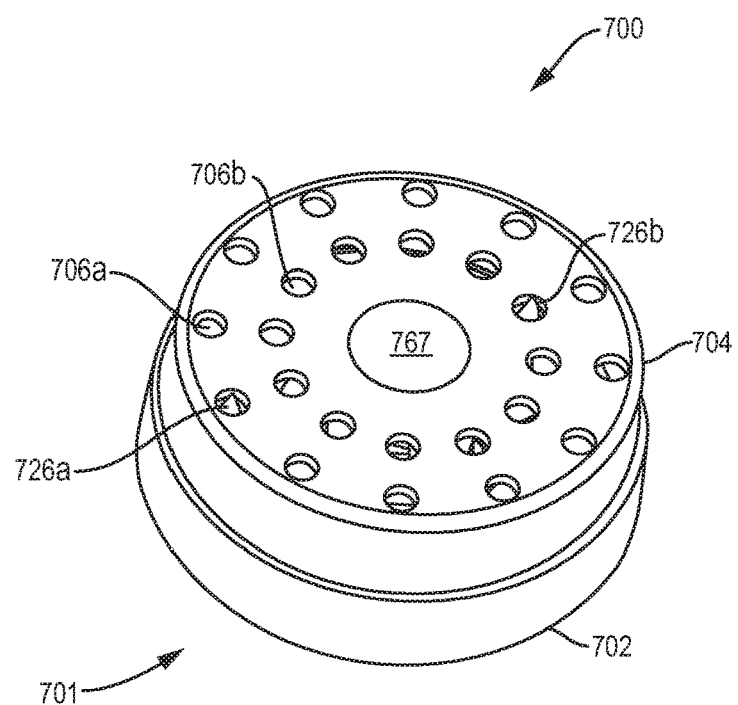
FIG. 7a illustrates a perspective view of an example of a vascular access port contemplated herein, with the needles in the retracted position.
Figure 7B:
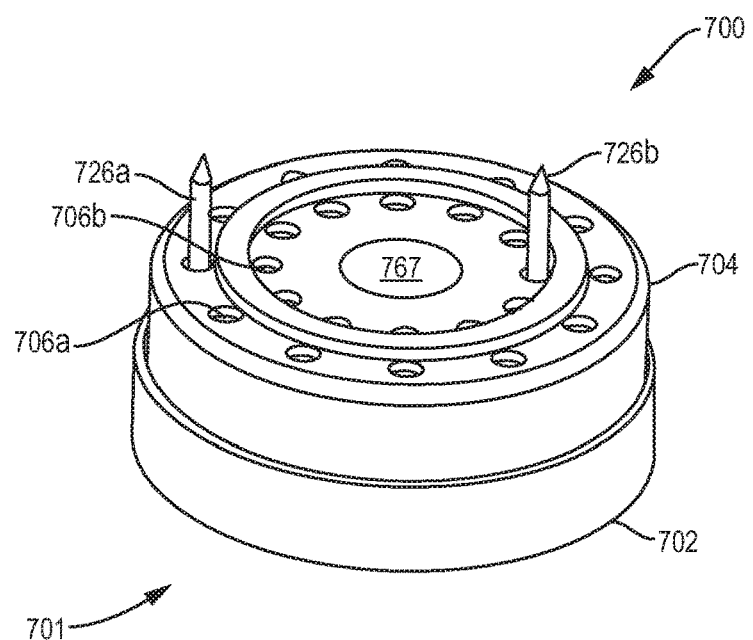
FIG. 7b illustrates a perspective view of an example of a vascular access port contemplated herein paired with an actuator, with the needles in the extended position.

FIGS. 7a and 7b illustrate another example of an access port 700 with a needle elevator mechanism 707 and needle shift mechanism 722. The access port 700 may include a body 701 comprising a cupped cylindrical base 702 supporting an overlying cylindrical cover 704. The cover 704 may include on the top surface/wall 704a a series of pre-defined openings 706a, 706b to allow the passage of needles 726a, 726b respectively, through the top wall 704a of the cover 704 to retract into and extend out of the body 701 of the access port 700.

In order to prevent access of body fluids and/or ingrowth of tissue into the openings 706a, 706b in the access port 700, the access port 700 may also be contained in a housing 703 (not shown, similar to housing 103), which may be made of a "self-healing" material, such as silicone. When extended, the needles 726a, 726b may pierce through the self-healing material. Thereafter, when the needles 726a, 726b are retracted, the openings 706a, 706b created in the self-healing material may sufficiently close (i.e. self-close) so that the access port 700 remains impervious to body fluids and ingrowth of body tissue. Alternatively, the cover 704, and more particularly the top wall 704a of the cover 704, may be made of a self-healing material, and the needles 726a, 726b may pierce through the top wall 704a of the cover 704.

Figure 7C:
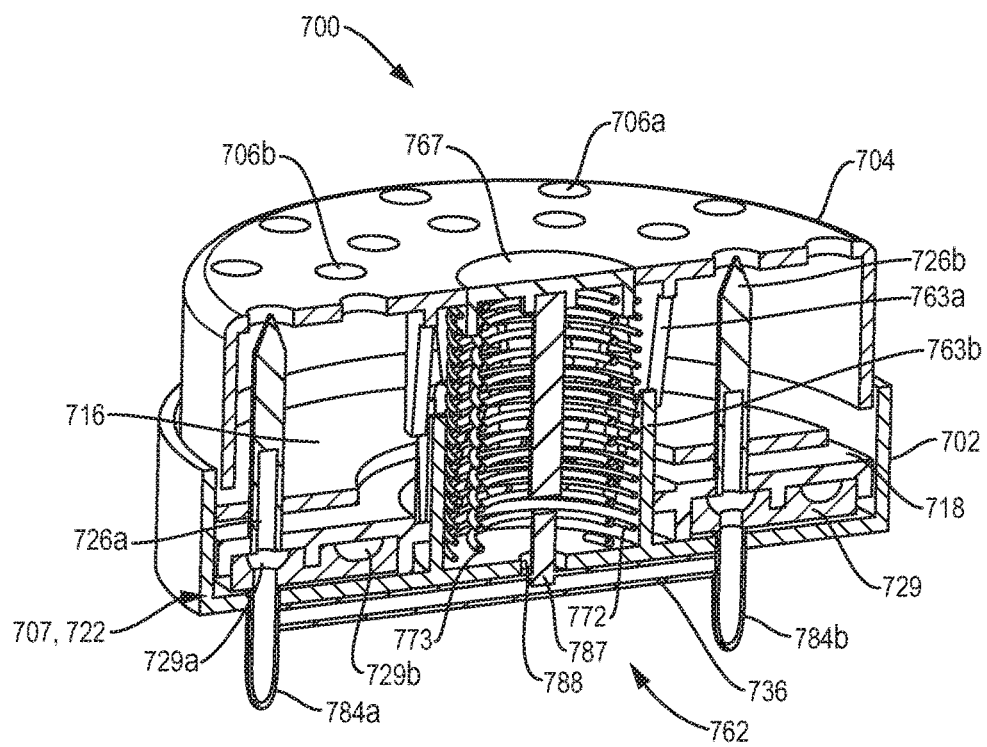
FIG. 7c illustrates a cross-sectional view of an example of the vascular access port shown in FIG. 7a, with the needles in the retracted position.

Referring to FIGS. 7b and 7c, inside the access port 700, the needles 726a, 726b may be supported by a needle support member 718, which generally has a shape of an annular plate. A circular ratcheting mechanism 762 is disposed in the center of the access port 700, which comprises an upper (top) annular cylindrical ratchet portion 762a disposed above a lower (bottom) annular cylindrical ratchet portion 762b, which engage and disengage from each other to change a circumferential (radial) position of the needles 726a, 726b. The upper ratchet portion 762a may have a cylindrical wall separate or integral to the cover 704, particularly extending transverse to the top wall 704a of the cover 704, with a plurality of downward pointing teeth 763a. Similarly, the lower ratchet portion 762b may have a cylindrical wall separate or integral to the base 702, particularly extending transverse to a bottom wall 702a of the base 702, with a plurality of upward pointing teeth 763b.

The needle support member 718 contains circular channels 729a, 729b in fluid communication with the lumens 727a, 727b of needles 726a, 726b, respectively, at the bottom surface of the needle support member 718, and in fluid communication with the lumen of the catheters 784a, 784b, respectively, that access the blood vessels of a patient. The circular channels may be defined by the bottom wall of the needle support member 718 in the form of two grooves in the bottom surface in which are fitted a circular ring 729 having also two circular grooves, hence defining channels 729a, 729b.

Figure 7D:
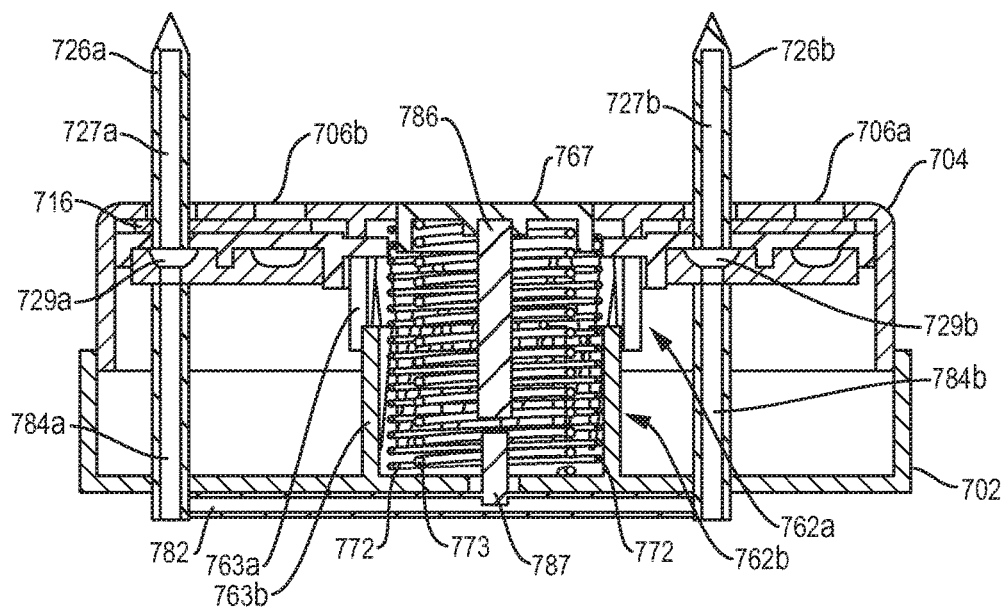
FIG. 7d illustrates a cross-sectional view of an example of the vascular access port shown in FIG. 7b, with the needles in the extended position.

Referring still to FIGS. 7b and 7d, when an actuator 740 comprising a magnet 741, such as a permanent magnet or an electromagnet, is applied by the medical personnel (e.g. physician, clinician) on the skin of the patient over the access port 700, it activates the needle elevator mechanism 707 by attracting the permanent magnet 716 of the access port 700, against the compression bias of outer coil spring 772 and raising the needle support member 718, along with extending needles 726a, 726b through respective openings 706a, 706b. Removal of the permanent magnet, or reversal of the electromagnet 741, will release the permanent magnet 716 and, with the decompression of outer coil spring 772 disposed inside the ratcheting mechanism, the needle support member 718 is returned to the bottom, with the needles 726a, 726b retracted inside the access port 700.

Medical personnel may then press the center button 767 to cause the teeth 763a of the upper ratchet portion 762a to engage with the teeth 763b of the lower ratchet portion 762b, forcing the lower ratchet portion 762b to rotate one notch at a time for each use of the access port 700, displacing with it the needle support member 718 circumferentially and thus positioning the needles 726a, 726b at a new circumferential (radial) position as described in relation to FIGS. 8a to 8d below. The medical personnel have the option of repeatedly depressing button 767 in order to further advance rotation of the needles 726a, 726b to other positions.

The details of the ratcheting mechanism are described in FIG. 7d. The access port 700 may include a button 767 at the center of cover 704. The button 767 is attached to a central push rod 786 and biased in the upward position by an inner coil spring 773. When the button 767 is depressed, the central push rod 786 shifts down and pushes a shutter 787 that extends through an opening 788 in the base 702 and collapse the wall of the catheter bridges 782, 783 (only one shown) connecting both catheters 784a, 784b. Push rod 786 is separate from shutter 787 to allow the button 767 to have a larger range of motion than required for shutter 787, easing use by the medial personnel. The purpose and operation of this system is reviewed in greater details with regard to FIGS. 9a to 9d below.

Figure 8A:
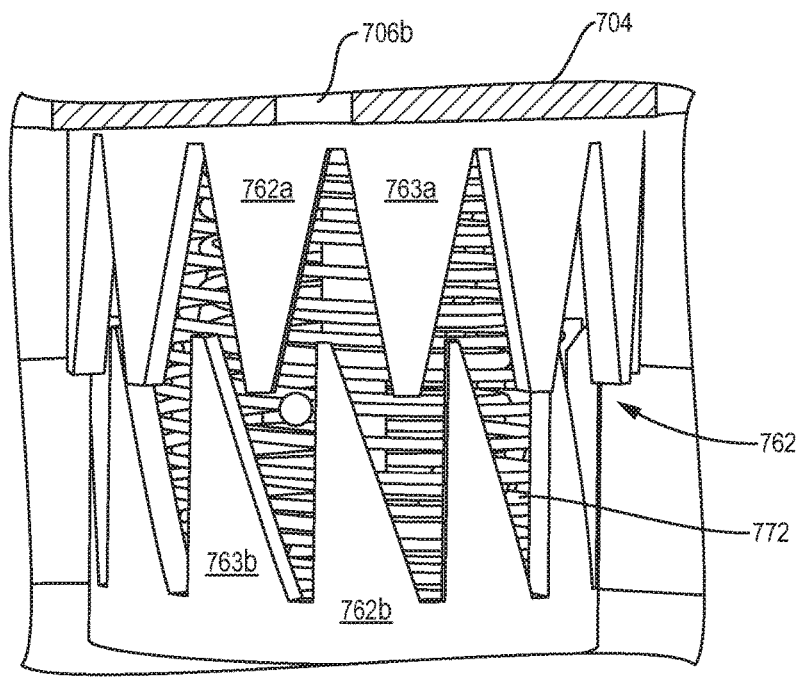
FIG. 8a illustrates a side view of an example of a ratcheting mechanism according to the vascular access port shown in FIGS. 7c-d.
Figures 8B, 8C, 8D:
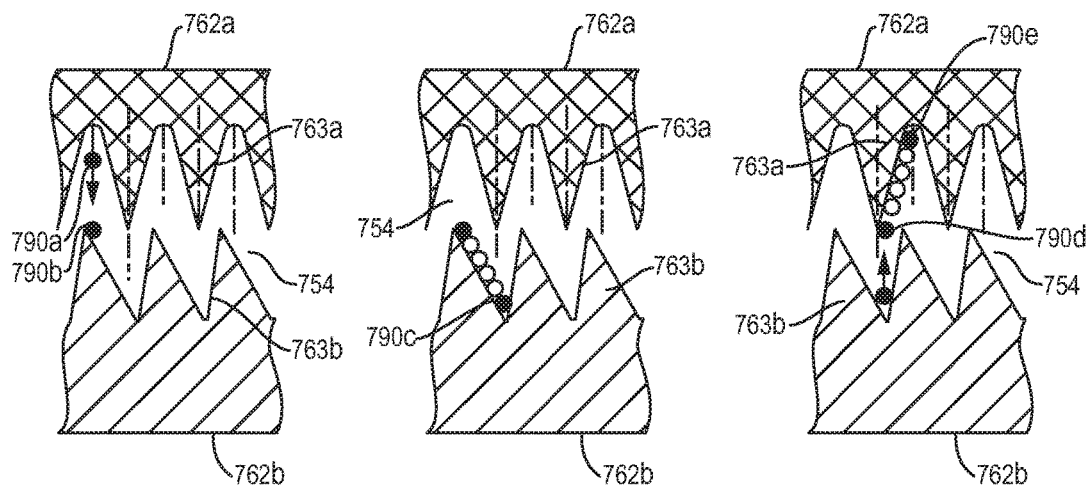

FIGS. 8a to 8d illustrate various stages of the operation of the ratcheting mechanism of access port 700. As shown in FIG. 8a, the upper ratchet portion 762a and the lower ratchet portion 762b of the ratcheting mechanism 762 are disposed around outer coil spring 772. In FIGS. 8b-8d, dots 790a to 790e illustrate the rotation of the lower ratchet portion 762b in relation to the upper ratchet portion 762a upon a downward motion of the needles 726a, 726b after an initial use of the access port 700. As shown, during operation, the bottom teeth 763b engage in an adjacent slot 754 between upper ratchet teeth 763a. The ratcheting action forces the upper ratchet teeth 763a to move the next position for engagement with the lower ratchet teeth 763b, and the coil spring 772 creates a torsional force as it is compressed by button 767 that will drive the upper ratchet portion 762a rotationally.

FIGS. 9a to 9d illustrate the operation of the button 767 of access port 700 as shown in FIG. 7d. As viewed in FIGS. 9a and 9b, the needles 726a, 726b of the access port 700 are functioning in a blood flow mode. The button 767 is in an upper position flush with the top surface of the cover 704, with central rod 786 being collinear with, but not engaging shutter 787. Valve 781*a* of needle 726*a* is open and against the wall of the needle 726*a*, and similarly, valve 781*b* of needle 726*b* is open and against the wall of the needle 726*b*. In this configuration the blood circulates out of needle 726*b*, and back into needle 726*a* as when the access port 700 is used for hemodialysis of a patient with kidney failure.

Figures 9A, 9B:
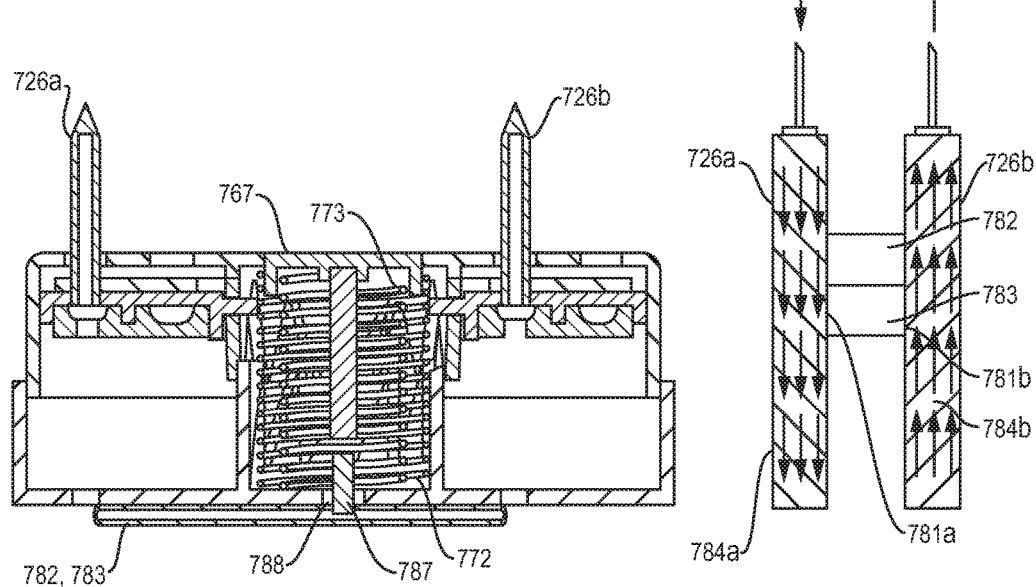
FIG. 9a illustrates a cross-section view of a vascular access port as shown in FIGS. 7a to 7d, in a blood flow mode.
FIG. 9b illustrates a side view of the operation of the needles of a vascular access port as shown in FIG. 9a, in a blood flow mode.
Figures 9C, 9D:
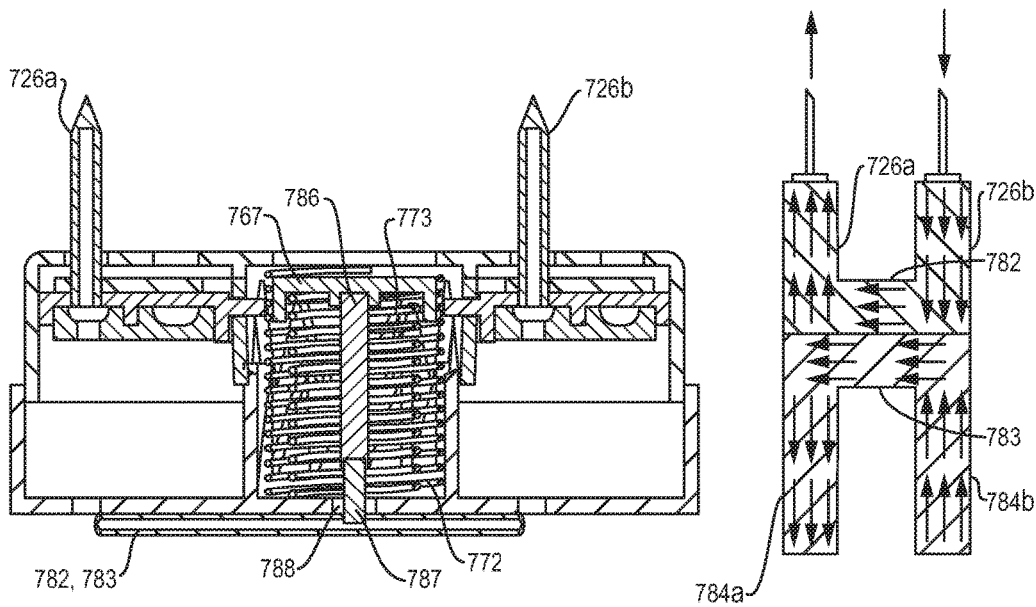
FIG. 9c illustrates a perspective view of a vascular access port as shown in FIGS. 7a to 7b, in a needle-cleaning mode.
FIG. 9d illustrates a side view of the operation of the needles of a vascular access port as shown in FIG. 9c, in a needle-cleaning mode.

As viewed in FIGS. 9*c* and 9*d*, the needles 726*a*, 726*b* of the access port 700 are functioning in a cleaning mode. The button 767 is in a depressed position. In this configuration the blood circulates in catheters 784*a*, 784*b* through bottom bridge catheter 783 and a cleaning solution may be circulated in needles 726*a*, 726*b* through upper bridge catheter 782. Valve 781*a* of needle 726*a* is closed and blocking the flow between the needle 726*a* and catheter 784*a*, and similarly, valve 781*b* of needle 726*b* is closed and blocking the flow between the needle 726*b* and catheter 784*b*.

Valves 781*a* and 781*b* for connection to catheters 784*a* and 784*b* respectively may be of any sliding or rotational design incorporated into the body of the access port 700 following well known engineering principles to provide the fluid controls described in FIG. 9*b* and FIG. 9*d*.

Figure 10A:
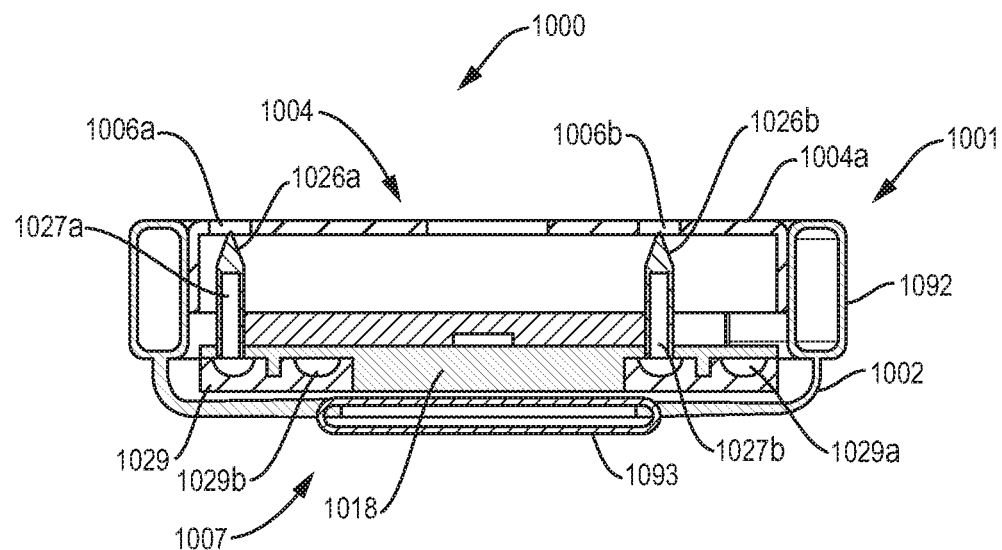
FIG. 10a illustrates a cross-sectional view of an example of a vascular access port contemplated herein, with the needles in the retracted position.
Figure 10B:
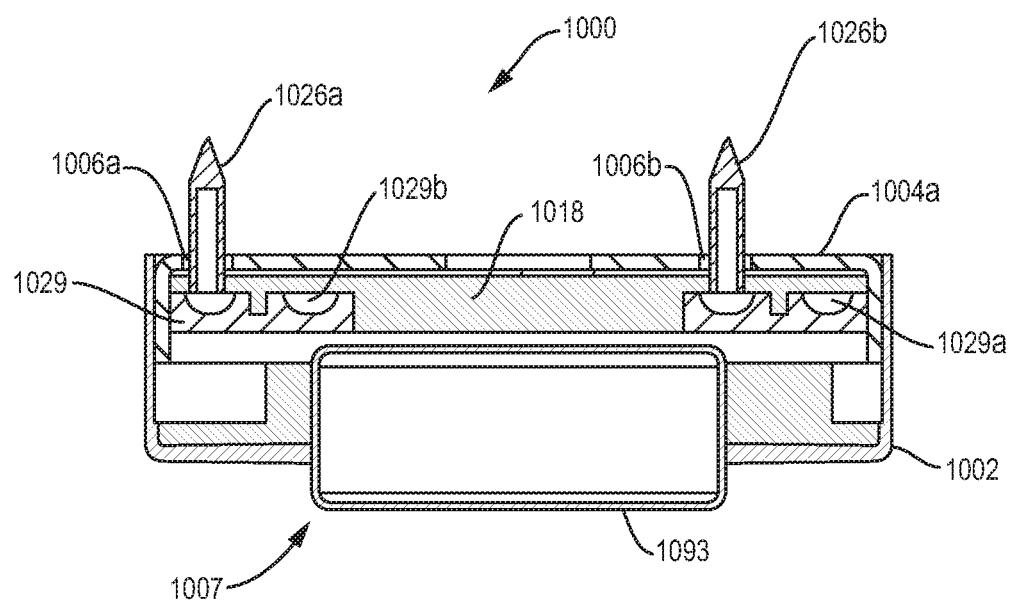
FIG. 10b illustrates a cross-sectional view of the vascular access port of FIG. 10a, with the needles in the extended position.

FIGS. 10*a* and 10*b*, illustrate another example of an access port 1000 with an alternate elevator mechanism 1007. The access port 1000 may include a body 1001 comprising a cylindrical base 1002 supporting an overlying cylindrical cover 1004. The cover 1004 may include on the top surface/wall 1004*a* a series of predefined openings 1006*a*, 1006*b* to allow the passage of needles 1026*a*, 1026*b* respectively, through the top wall 1004*a* of the cover 1004 to retract into and extend out of the body 1001 of the access port 1000.

In order to prevent access of body fluids and/or ingrowth of tissue into the openings 1006*a*, 1006*b* in the access port 1000, the access port 1000 may also be contained in a housing 1003 (not shown, similar to housing 103), which may be made of a "self-healing" material, such as silicone. When extended, the needles 1026*a*, 1026*b* may pierce through the self-healing material. Thereafter, when the needles 1026*a*, 1026*b* are retracted, the openings 1006*a*, 1006*b* created in the self-healing material may sufficiently close (i.e. self-close) so that the access port 1000 remains impervious to body fluids and ingrowth of body tissue. Alternatively, the cover 1004, and more particularly the top wall 1004*a* of the cover 1004, may be made of a self-healing material, and the needles 1026*a*, 1026*b* pierce through the top wall 1004*a* of the cover 1004.

Inside the access port 1000, the needles 1026*a*, 1026*b* may be supported by a needle support member 1018. The needle support member 1018 contains circular channels 1029*a*, 1029*b* in fluid communication with the lumens 1027*a*, 1027*b* of needles 1026*a*, 1026*b*, respectively, at the bottom surface of the needle support member 1018, and to the lumen of the catheters that access the blood vessels of a patient (not shown). The circular channels 1029*a*, 1029*b* may be defined by the bottom wall of the needle support member 1018 in the form of two grooves in the bottom surface in which are fitted a circular ring 1029 having also two circular grooves, hence defining channels 1029*a*, 1029*b*.

In operation, the elevator mechanism 1007 of the vascular access port 1000 may be activated to raise the needles 1026*a*, 1026*b* by medical personnel squeezing the sides of the vascular access port 1000, on the side inflatable/deflatable balloons 1092 (as shown in FIG. 10*a*) shifting air or gas or a fluid contained therein to a bottom balloon 1093 (as shown in FIG. 10*b*). Inflation of balloon 1092 raises needle support member 1018, forcing needles 1026*a*, 1026*b* though openings 1006*a*, 1006*b*. An opening 1094 at the center of the top wall 1004*a* of the cover 1004, may be used to place a ratcheting mechanism to move the circumferential (radial) position of the needles inside the access port 1000, as well as a valve activating system to allow cleaning of the needle as previously described above.

Figure 11:
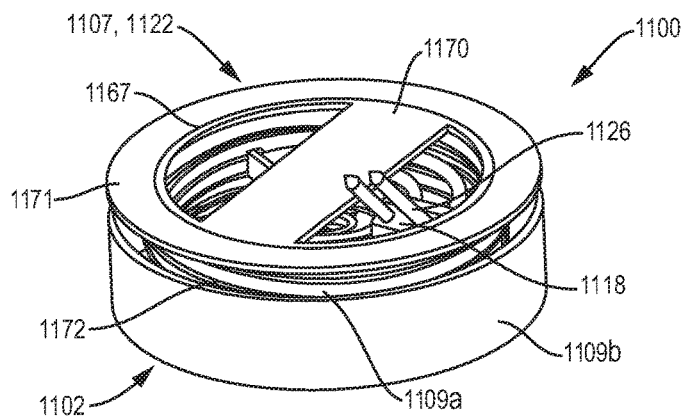
FIG. 11 illustrates a perspective view of an example of a vascular access port contemplated herein, with the needles in the extended position.
Figure 12:
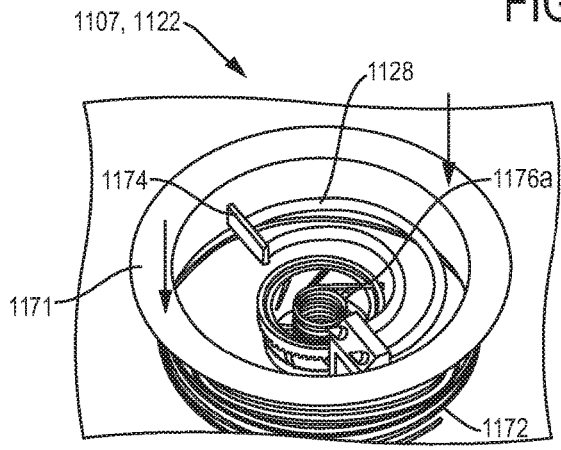
FIG. 12 illustrates a perspective view of the ratcheting mechanism as shown in FIG. 11, with the needles in the retracted position.
Figure 13:
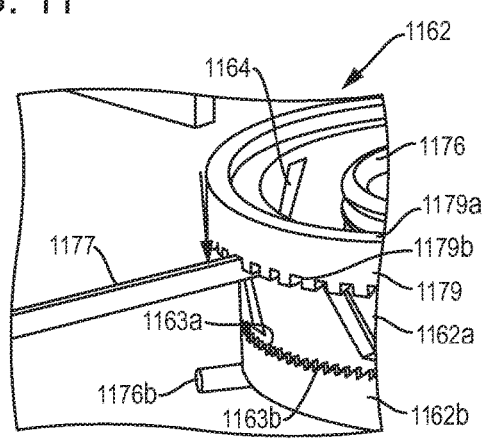
FIG. 13 illustrates a perspective view of a portion of the ratcheting mechanism as shown in FIG. 12, with the needle in the retracted position.

FIGS. 11 to 13 illustrate another example of an access port 1100 with a needle elevator mechanism 1107 and needle shift mechanism 1122. In this example, the cover has been removed to expose the needle elevator mechanism 1107 and needle shift mechanism 1122. Cylindrical member 1109 may comprise an inner cylindrical member 1109*a* and an outer cylindrical member 1109*b* having a coil spring 1172 located there between. As shown, inner cylindrical member 1109*a* has a flange 1171 disposed over coil spring 1172 such that coil spring 1172 biases downward movement of inner cylindrical member 1109*a*.

Needle shift mechanism 1122 may more particularly be provided by a circular ratcheting mechanism 1162, which may be activated by a button 1167 disposed in inner cylindrical member 1109*a*. The button 1167 may include a cross-member/bridge 1170 that spans the diameter of the inner cylindrical member 1170 and is connected thereto by an annular ring. Inside the access port 1100, the needles 1126 may be supported by a needle (arm) support member 1118 that is connected to a lower (bottom) annular cylindrical ratchet portion 1162*b* of a ratcheting mechanism 1162. Referring to FIG. 12, the needle support member 1118 may contain channels connected to the needle shafts 1128 at one end and to the vascular catheters (not shown) at catheter inlets (not shown) at the other end. The needles 1126 may also include shafts 1128 supported by arm 1174.

Referring to FIG. 13, the ratcheting mechanism 1162 may also include an upper (top) ratchet portion 1162*a* disposed above lower (bottom) annular cylindrical ratchet portion 1162*b*. The upper (top) ratchet portion 1162*a* may have a cylindrical wall with a series of elongated openings 1164 for receiving a bar 1177 which connects inner cylindrical member 1109*a* to circular outer ratchet 1179 of the ratcheting mechanism 1162. The ratcheting mechanism 1162 may include a torsion spring 1176, with a top end 1176*a* engaged in the outer ratchet 1179, and the bottom end 1176*b* engaged with the bottom ratchet portion 1162*b*.

Referring to FIGS. 12 and 13, when the flange 1171 is depressed by the medical personnel, it triggers the elevator mechanism 1107 of the ratcheting mechanism 1162 to shift (rotate) the position of the needles 1126 up through the needle support member 1118. The ratcheting mechanism 1108 shifts (rotates) the needle support member 1118 clockwise forcing the needle shafts 1128 to slide through throughholes 1119 formed in the needle support member 1118. Because the through-holes 1119 are oblique, the needles 1126 are elevated. When the button 1167 is depressed, it activates the needle-shift mechanism 1122 such that the bar 1177 slides in one of the elongated openings slits 1164, rotating clockwise the upper (top) ratchet portion 1162*a* as the bar 1177 shifts downward disengaging from teeth 1179*b* the outer ratchet 1179. The ratchet teeth 1163*a* of the upper (top) ratchet portion 1162*a* engage with the ratchet teeth 1163*b* of the lower (bottom) ratchet portion 1162*b* forcing both upper (top) ratchet portion 1162*a* and lower (bottom) ratchet portion 1162*b* to rotate together, displacing the needles 1126 out of the needle support member 1118. Outer ratchet 1179 serves to prevent the torsion spring 1176 from releasing until sufficient energy is stored in the torsion spring 1176 to drive the needles 1126 upward.

Figure 14A:
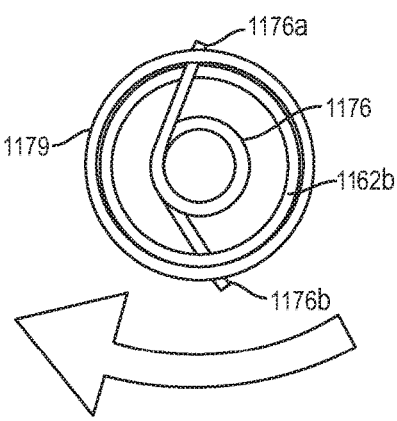
FIGS. 14a and 14b illustrate top views of the configurations of a torsion spring used in the ratcheting mechanism as shown in FIG. 12.
Figure 14B:
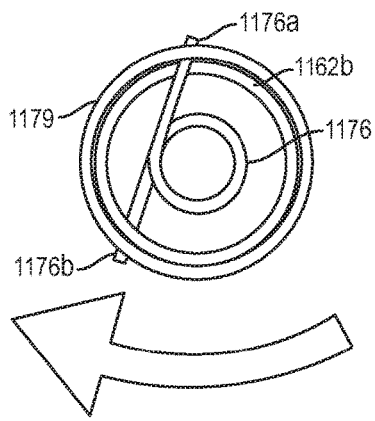

FIGS. 14*a* and 14*b* illustrate top views of the configurations of a torsion spring used in the ratcheting mechanism as shown in FIG. 12. When button 1167 is depressed, a clockwise rotational force of both the upper (top) ratchet portion 1162a and lower (bottom) ratchet portion 1162b, together, is applied to the bottom end 1176b of the torsion spring 1176. When button 1167 is depressed a sufficient number of times, the ratcheting mechanism 1162 will release the torsion spring 1176 to drive the needles 1126 upward. FIG. 14a to FIG. 18c illustrate this process. When button 1167 is depressed lower (bottom) ratchet portion 1162b is rotated clockwise relative to outer ratchet 1179, which includes one end 1176b of torsion spring 1176 causing energy to be stored in torsion spring 1176. Referring to FIG. 15, the needle shaft supporting arm 1174 is connected to an uppermost ring 1195 which provides access for cannula connections (not shown). Needles shafts 1128 schematically illustrate that a connection is to be provided between the supporting arm 1174 and needles 1126. Needle shafts 1128 may be made of a suitable flexible or extendable material to allow the movement of needle to occur.

FIG. 16 illustrates a partial perspective view of the ratcheting mechanism 1162 as shown in FIG. 12, with the needle 1126 in the retracted position. Outer ratchet 1179 rotates clockwise relative to upper (top) ratchet portion 1162a as button 1167 is depressed causing the ratcheting mechanism 1162 to be driven.

Figure 18A:
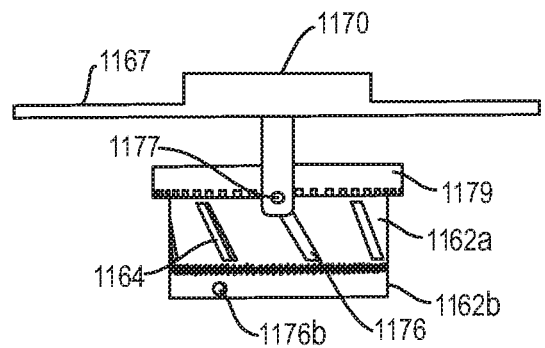
FIGS. 18a to 18c illustrate side views of the various configurations of the ratcheting mechanism as shown in FIG. 12.
Figure 18B:
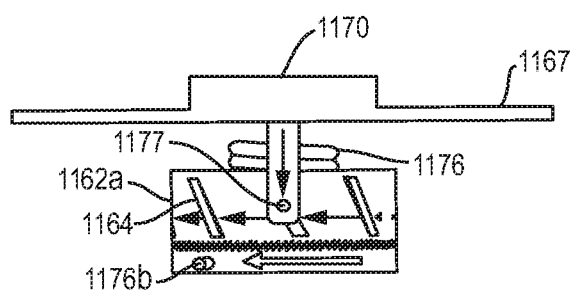
Figure 18C:
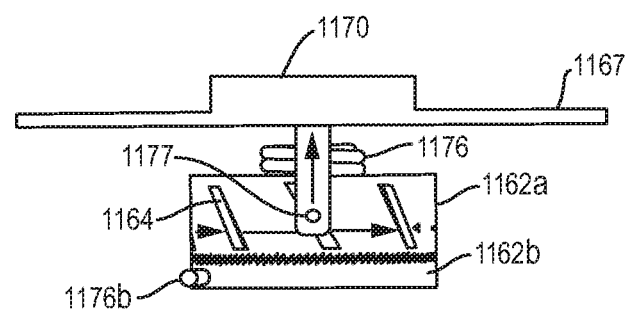

FIGS. 17a and 17b illustrate top views of the configurations of a torsion spring 1176 used in the ratcheting mechanism 1162 as shown in FIG. 12 when a clockwise rotation force by the outer ratchet 1179 is applied to the top end 1176a of the torsion spring 1176. When the torsion spring 1176 is sufficiently energized the ratcheting mechanism 1162 has rotated such that locking bar 1177 is released. The needles 1126 are driven forward by the movement of the torsion spring end 1176a relative to the other end 1176b of the torsion spring 1176, causing the needles to move out of the port body 1101. FIGS. 18a to 18c illustrate side views of the configurations of the ratcheting mechanism 1162 as shown in FIG. 12.

Figure 19:
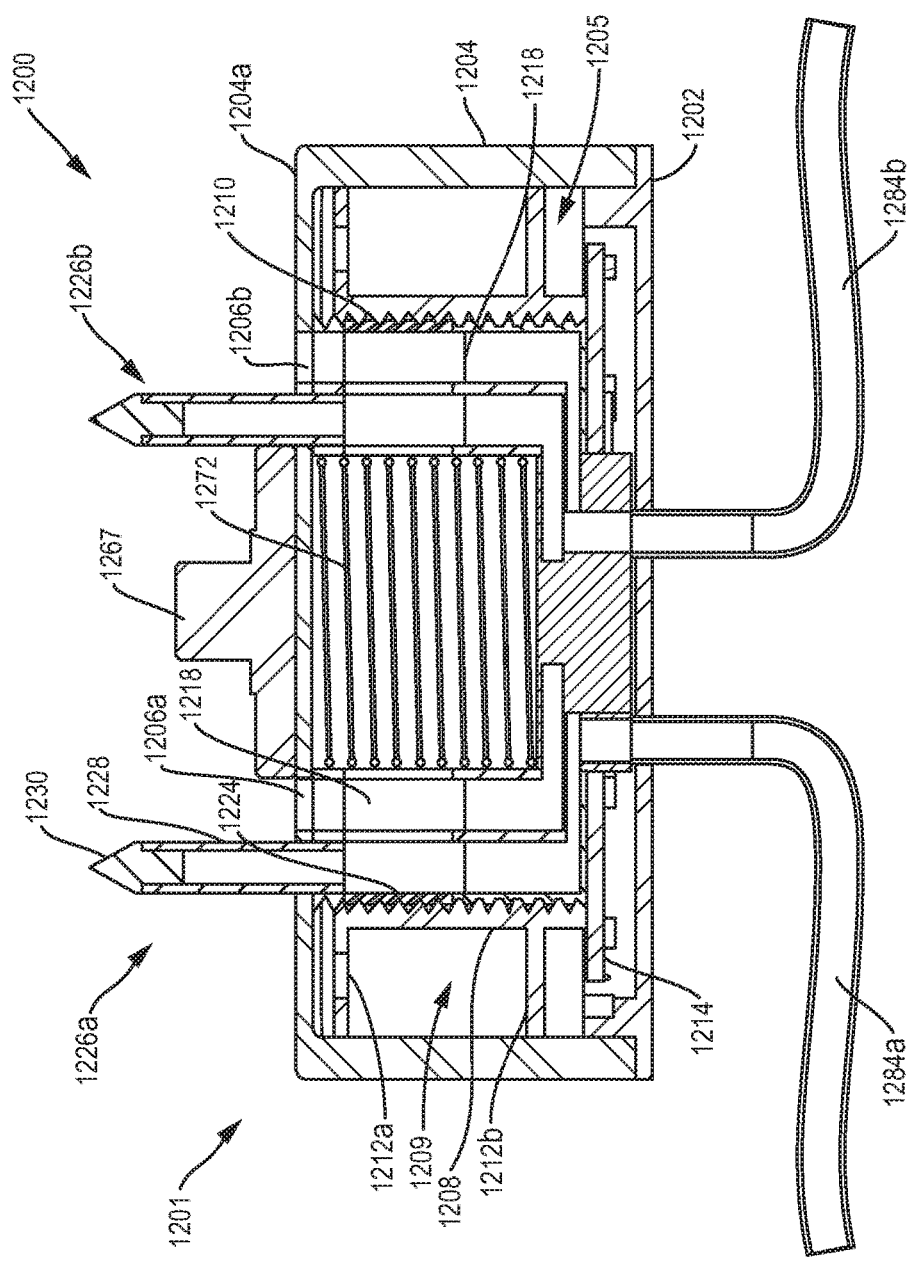
FIG. 19 illustrates a cross-sectional view of an example of a vascular access port contemplated herein, with the needles in extended position, and flow path open.
Figure 20:
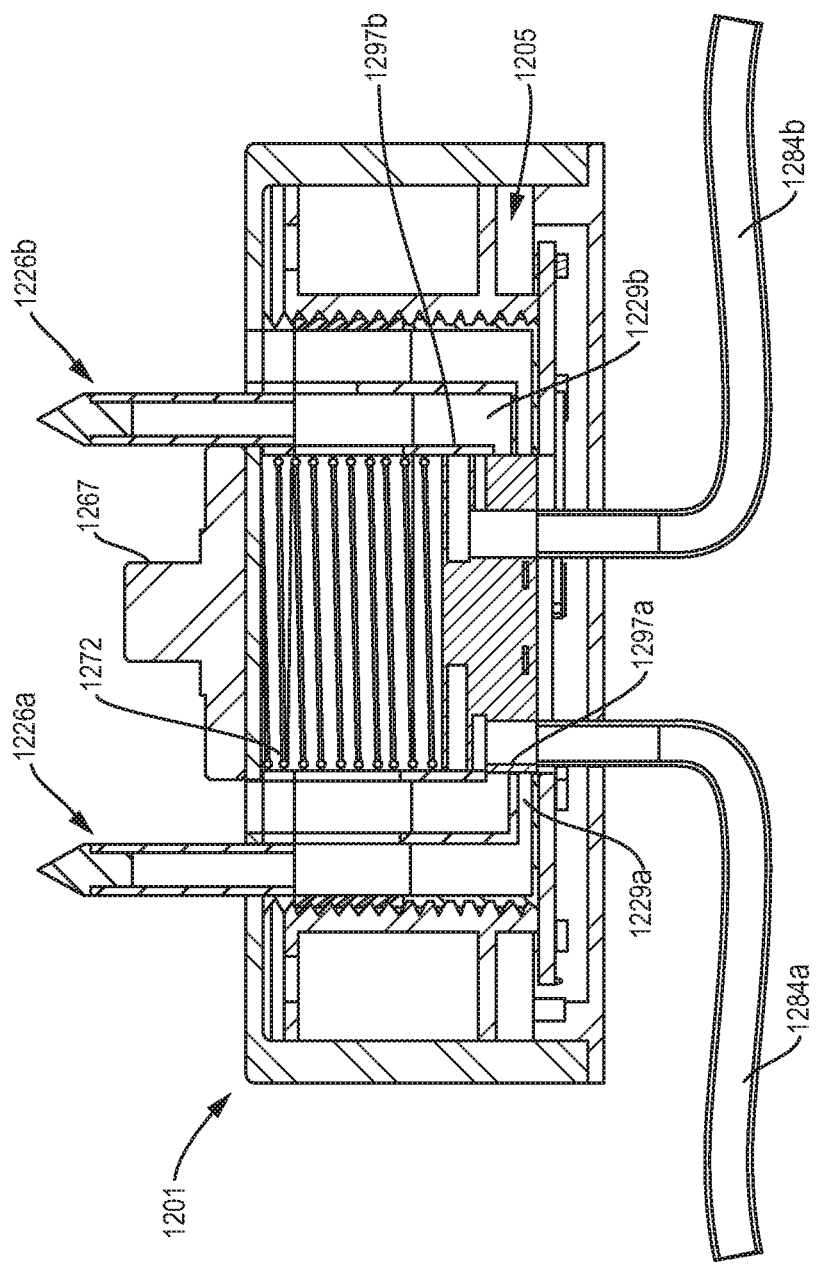
FIG. 20 illustrates a cross-sectional view of the vascular access port of FIG. 19, with the needles in extended position, and flow path closed.

FIGS. 19 and 20 illustrate the operation of an access port 1200 to open or close flow of fluid through the access port 1200. FIG. 19 illustrates the access port 1200 in an open configuration where fluid or blood can flow from the opening of the needles 1226 through the port and into the body catheters. The access port 1200 may include a body 1201 comprising a base 1202, generally having a shape of a circular plate, supporting an overlying cover 1204, which cooperate to form an inner cavity 1205. The cover 1204 may have on the top surface/wall 1204a a series of predefined openings 1206a, 1206b to allow the passage of needles 1226a, 1226b through the top wall 1204a of the cover 1204 to retract into and extend out of the body 1201 of the access port 1200.

In order to prevent access of body fluids and/or ingrowth of tissue into the openings 1206a, 1206b in the access port 100, the access port 1200 may be contained in a housing 1203 (not shown, similar to housing 103), which may be made of a "self-healing" material, such as silicone. When extended, the needles 1226a, 1226b may pierce through the self-healing material. Thereafter, when the needles 1226a, 1226b are retracted, the openings 1206a, 1206b created in the self-healing material may sufficiently close (i.e. self-close) so that the access port 1200 remains impervious to body fluids and ingrowth of body tissue. Alternatively, the cover 1204, and more particularly the top wall 1204a of the cover 1204, may be made of a self-healing material, and the needles 1226a, 1226b may pierce through the top wall 1204a cover 1204. The openings 1206a, 1206b created in the self-healing material closes upon retraction of the needles 1226a, 1226b so that the access port 1200 remains impervious to body fluids and ingrowth of body tissue.

As with previous embodiments, the cavity 1205 of the access port 1200 contains a needle elevator mechanism 1207, which comprises a cylindrical (elevator) member 1209, which rests and rotates on circular floor 1214. As explained with previous embodiments, the floor 1214 of the needle elevator mechanism 1207 may also operate as part of a needle shift mechanism 1222. The base 1202 supports floor 1214 and provides the structural foundation for the needle elevator mechanism 1207 and the needle shift mechanism 1222, as well as forms part of the needle shift mechanism 1222.

Cylindrical (elevator) member 1209 of the needle elevator mechanism 1207 comprises a cylinder 1208 which may include internal threads 1210, as well as outer peripheral flanges 1212, provided by upper flange 1212a and lower flange 1212b. The flanges 1212a, 1212b may be used to hold at least one permanent magnet 1216 in a fixed position there between.

The needle elevator mechanism 1207 further comprises a needle support member 1218. The access port needles 1226a, 1226b are secured to (fastened) and supported within the interior of the cylinder 1208 by the needle support member 1218, which generally has a shape of an annular plate. The needle support member 1218 may have external threads 1224 on the periphery that engages the internal threads 1210 of the cylinder 1208. Each needle 1226a, 1226b may include a shaft 1228 for connecting through a fluid path with internal catheters 1284a, 1284b accessing the blood vessel, and removable a tip 1230 which allows access to the lumen 1227 of the needles 1226a, 1226b for the passage of fluids or blood.

FIG. 20 illustrates the access port 1200 in a close configuration where fluid or blood cannot flow through the access port 1200. At the center of the vascular access port 1200, a valve mechanism may be used by the medical personnel to open or close the flow of fluid through the access port 1200. A coil spring 1272 may be compressed by depressing button 1267, sliding valves 1297a, 1297b to close channels 1229a, 1229b.

The needles contemplated herein, may include any hollow cylinder or shaft. The needle may include, in some examples, standard bevels, short bevels, true short bevels, etc. Furthermore, the needles may exhibit an outer diameter in the range of 0.1 mm to 4.6 mm, including all values and increments therein. In addition, the needle may exhibit an inner diameter in the range of 0.08 mm to 4.0 mm, including all values and increments therein. Furthermore, the needles may exhibit a nominal wall thickness in the range of 0.002 mm to 0.4 mm including all values and increments therein. The needles may be formed of stainless steel, ceramic composites, or other materials. In addition, the needles or the needle tips may be replaceable in case of dulling.

Accordingly, a method of injecting a composition into a subject may be provided using the access port described herein. Once the port with at least one needle has been implanted in the patient and at least one internal catheter has been inserted into a vascular vein or body channel of a patient in need of the repeated systemic or local therapy, the access port may be accessed and therapy delivered according to the following steps. Medical personnel apply an actuator over the access port and activate the elevator mechanism in the direction that will raise the at least one needle out through the cover of the access port, piercing the skin at a first location. The actuator is put aside. The at least one needle is then connected to an syringe, or bag containing the composition through appropriate tubing or catheter. The composition is injected as a bolus or drip, or infused at the prescribed rate. Once the therapy has been delivered, the actuator is placed again over the access port and activated in a reversed direction that lowers the at least one needle under the skin and into the access port, under the cover. The actuator is maintained until the actuator engages the needle shift mechanism to displace the at least one needle from the position just used to a new position inside the access port such that when the access port is accessed again at the next therapy session, the needle will protrude at a new location.

A composition may include pharmaceuticals, nutrients, contrasting agents, blood or blood components, such as plasma, platelets, white blood cells, red blood cells, etc. Furthermore, a patient may include any vertebrate or invertebrate, including humans, other mammals, apes, domestic animals, cattle, etc. A vascular access port may be implanted into the patient and the catheter may be inserted into a vein. The needle may be extended from the port upon actuation and may puncture the skin. A composition may be introduced to the subject by either injecting the composition into the needle or otherwise introducing the needle into a container, such as through a vial stopper. Once administration of the composition is finished, the needle may be retracted or otherwise positioned back through the skin and into the port.

Alternatively, vascular access ports as described herein are suitable for use in hemodialysis of patient in need thereof, including patients in renal kidney failure and end stage renal disease. Once the vascular access port with at least two needles has been implanted in the patient and at least two internal catheters have been inserted into a vascular vein of a patient in need of the repeated hemodialysis, the port may be access and therapy performed according to the following steps. A medical personnel, apply an actuator over the vascular access port and activate the elevator mechanism in the direction that will raise the at least two needles out through the cover of the vascular access port, piercing the skin at a first location. The actuator is put aside. The at least two needles are then connected to a hemodialysis machine through appropriate tubing or catheters, one to receive the blood to be purified or filtered, the other to return the clean blood to the patient. Once the therapy has been delivered, the actuator is placed again over the vascular access port and activated in a reversed direction that lowers the at least two needles under the skin and into the vascular access port, under the cover. The actuator is maintained until the actuator engages the needle shift mechanism to displace the at least two needles from the position just used to a new position inside the vascular access port such that when the vascular access port is accessed again at the next therapy session, the needles will protrude at a new location.

The vascular access port described herein may be modified to define one of the possible circumferential (radial) positions of the needles to perform routine maintenance of the vascular access port. For example, the needles may be made of a conductive material, and when occupying the maintenance position, become connected to wiring that feeds a battery or a microprocessor in the vascular access port. The needles can then be connected to a power supply to recharge the vascular access port battery, to a computer for data transfer from a microprocessor in the vascular access port, or to control inputs for the operation of the vascular access port by a microprocessor.

The battery may be useful in a vascular access port that operates the needles extraction/retraction as well as rotation through a motor. Also, the battery may power a drug dispensing pump or other such mechanism that provides a release of a composition to the patient. Batteries may also be used to power implantable sensors or devices to transmit or receive information that provide diagnostic information to a clinician or still further another implantable device. Such information provided may include operational information on the vascular port, such as the position of needles in the port, the number of uses the port has experienced, the time between uses, etc. A vascular port may include a microprocessor so as to provide storage and processing of such information, programmable control of flow through the port or other such operations, means of preventing inadvertent operation of the port by requiring recognition of security passwords or for other means that my provide useful interaction with the port, external devices or with the clinician, however indirectly.

Alternatively, the needles may include removable and replaceable tips that allow electrical connection inside the needle body. Such tips may be reused after appropriate cleaning or preferably exchanged for sterilized replacements. Electrical connections may be made directly with the tips or via a mechanism exposed after tips are removed.

One or more maintenance positions may be used also to deliver chemicals to resupply a reservoir in the vascular access port that time-releases medicine to the patient, or that feeds a chemical battery, such as a fuel cell. The needles can then be connected to a separate channel that leads to the reservoir, or battery. In some embodiments, the chemical may be a gas for use in establishing pressure, such as to operate a pump that time-releases drug to the patient.

Alternatively, a maintenance position may be used to deliver a device to the vascular access port, such as replacement of a battery, vascular access port parts, RFID chips, microprocessors, encapsulated drugs, and the like.

To perform a maintenance operation, medical personnel, apply an actuator over the vascular access port and activate the port in the direction which will engage the needle shift mechanism to position the at least one needle at the maintenance location. Then, the actuator is then set to engage the elevator mechanism to raise the at least one needle out through the cover of the vascular access port, piercing the skin at the maintenance location. The actuator is put aside. The at least one needle is then used to performed the required maintenance as described above. Once the maintenance operation has been performed, the actuator is placed again over the access port and activated in a reversed direction that lowers the at least one needle under the skin and into the access port, under the cover. The actuator is maintained to operate the actuator to engage the needle shift mechanism to displace the at least one needle from the position just used to a new position inside the port such that when the vascular access port is accessed again at a therapy session, the needle will protrude at a location designated for performing the required therapy.

The foregoing description of several methods and embodiments has been presented for purposes of illustration. It is not intended to be exhaustive or to limit the claims to the precise steps and/or forms disclosed, and obviously many modifications and variations are possible in light of the above teaching. For example, other elevator mechanisms have been previously described in U.S. Pat. No. 8,377,034 which is incorporated herein by reference in its entirety. Such elevator mechanism may be used in the vascular access port described herein interchangeably. It is intended that the scope of the invention be defined by the claims appended hereto.

What is claimed is:

1. A method of treating a subject, comprising:
penetrating a first needle outwardly through skin of the subject from within the subject from a first needle first use position of an access port implanted within the subject such that the first needle is exposed outside the subject,
   wherein the access port comprises an access port body containing the first needle and a needle shift mechanism, the needle shift mechanism movable within the access port body to move the at least one needle to a plurality of different use positions of the access port body, wherein the needle shift mechanism is rotatable around an axis of rotation, and the at least one needle is extendable and retractable along the axis of rotation; and
   wherein penetrating the first needle outwardly through skin of the subject is performed while extending the at least one needle along the axis of rotation;
introducing a first fluid into the subject through the first needle;
withdrawing the first needle inwardly through the skin of the subject from outside the subject such that the first needle is concealed within the subject and within the access port body, wherein withdrawing the first needle inwardly though the skin of the subject is performed while retracting the at least one needle along the axis of rotation;
moving the first needle within the access port body from the first needle first use position to a first needle second use position by rotating the needle shift mechanism around the axis of rotation;
penetrating the first needle outwardly through the skin of the subject from within the subject from the first needle second use position of the access port implanted within the subject such that the first needle is exposed outside the subject, wherein penetrating the first needle outwardly through skin of the subject is performed while extending the at least one needle along the axis of rotation;
introducing a second fluid into the subject through the first needle and;
withdrawing the first needle inwardly through the skin of the subject from outside the subject such that the first needle is concealed within the subject and within the access port body,
wherein withdrawing the first needle inwardly though the skin of the subject is performed while retracting the at least one needle along the axis of rotation.

2. The method claim 1 wherein:
the first needle comprises a first needle removable needle tip and a first needle shaft, and
wherein the first needle removable needle tip is removably secured to the first needle shaft, and
wherein the first needle removable needle tip closes a lumen of the first needle shaft to passage of fluid when secured to the first needle shaft; and further comprising
penetrating the first needle outwardly through the skin of the subject from within the subject from the first needle first use position of the access port implanted within the subject such that the first needle removable needle tip is exposed outside the subject.

3. The method claim 2 further comprising:
removing the first needle removable needle tip from the first needle shaft to access the lumen of the first needle shaft before introducing the first fluid into the subject through the first needle.

4. The method claim 3 further comprising:
replacing the first needle removable needle tip on the first needle shaft after introducing the first fluid into the subject through the first needle.

5. The method claim 4 wherein:
the first needle removable needle tip is replaced on the first needle shaft with the same removable needle tip removed from the shaft.

6. The method claim 4 wherein:
the first needle removable needle tip is replaced on the first needle shaft with a sterilized removable needle tip.

7. The method claim 4 further comprising:
penetrating the first needle outwardly through the skin of the subject from within the subject from the first needle second use position of the access port implanted within the subject such that the first needle removable needle tip is exposed outside the subject.

8. The method claim 7 further comprising:
removing the first needle removable needle tip from the first needle shaft to access the lumen of the first needle shaft before introducing the second fluid into the subject through the first needle.

9. The method claim 8 further comprising:
replacing the first needle removable needle tip on the first needle shaft after introducing the second fluid into the subject through the first needle.

10. The method claim 9 wherein:
the first needle removable needle tip is replaced on the first needle shaft with the same removable needle tip removed from the shaft.

11. The method claim 9 wherein:
the first needle removable needle tip is replaced on the first needle shaft with a sterilized removable needle tip.

12. The method claim 1 further comprising:
moving the first needle within the access port body from the first needle second use position to a first needle third use position.

13. A method of treating a subject, comprising:
penetrating a first needle outwardly through skin of the subject from within the subject from a first needle first use position of an access port implanted within the subject such that the first needle is exposed outside the subject,
   wherein the access port comprises an access port body containing the first needle and a needle shift mechanism, the needle shift mechanism movable within the access port body to move the at least one needle to a plurality of different use positions of the access port body, wherein the needle shift mechanism is rotatable around an axis of rotation, and the at least one needle is extendable and retractable along the axis of rotation; and
   wherein penetrating the first needle outwardly through skin of the subject is performed while extending the at least one needle along the axis of rotation;
removing a first fluid from the subject through the first needle;
withdrawing the first needle inwardly through the skin of the subject from outside the subject such that the first needle is concealed within the subject and within the access port body, wherein withdrawing the first needle inwardly though the skin of the subject is performed while retracting the at least one needle along the axis of rotation;
moving the first needle within the access port body from the first needle first use position to a first needle second use position by rotating the needle shift mechanism around the axis of rotation;
penetrating the first needle outwardly through the skin of the subject from within the subject from the first needle second use position of the access port implanted within the subject such that the first needle is exposed outside the subject, wherein penetrating the first needle outwardly through skin of the subject is performed while extending the at least one needle along the axis of rotation;
removing a second fluid from the subject through the first needle and;
withdrawing the first needle inwardly through the skin of the subject from outside the subject such that the first needle is concealed within the subject and within the access port body, wherein withdrawing the first needle inwardly though the skin of the subject is performed while retracting the at least one needle along the axis of rotation.

14. The method claim 13 wherein:
the first needle comprises a first needle removable needle tip and a first needle shaft, and
wherein the first needle removable needle tip is removably secured to the first needle shaft, and
wherein the first needle removable needle tip closes a lumen of the first needle shaft to passage of fluid when secured to the first needle shaft; and further comprising
penetrating the first needle outwardly through the skin of the subject from within the subject from the first needle first use position of the access port implanted within the subject such that the first needle removable needle tip is exposed outside the subject.

15. The method claim 14 further comprising:
removing the first needle removable needle tip from the first needle shaft to access the lumen of the first needle shaft before removing the first fluid from the subject through the first needle.

16. The method claim 15 further comprising:
replacing the first needle removable needle tip on the first needle shaft after removing the first fluid from the subject through the first needle.

17. The method claim 16 wherein:
the first needle removable needle tip is replaced on the first needle shaft with the same removable needle tip removed from the shaft.

18. The method claim 16 wherein:
the first needle removable needle tip is replaced on the first needle shaft with a sterilized removable needle tip.

19. The method claim 16 further comprising:
penetrating the first needle outwardly through the skin of the subject from within the subject from the first needle second use position of the access port implanted within the subject such that the first needle removable needle tip is exposed outside the subject.

20. The method claim 19 further comprising:
removing the first needle removable needle tip from the first needle shaft to access the lumen of the first needle shaft before removing the second fluid from the subject through the first needle.

21. The method claim 20 further comprising:
replacing the first needle removable needle tip on the first needle shaft after removing the second fluid from the subject through the first needle.

22. The method claim 21 wherein:
the first needle removable needle tip is replaced on the first needle shaft with the same removable needle tip removed from the shaft.

23. The method claim 21 wherein:
the first needle removable needle tip is replaced on the first needle shaft with a sterilized removable needle tip.

24. The method claim 13 further comprising:
moving the first needle within the access port body from the first needle second use position to a first needle third use position.

* * * * *

UNITED STATES PATENT AND TRADEMARK OFFICE
CERTIFICATE OF CORRECTION

PATENT NO. : 10,369,345 B2  
APPLICATION NO. : 15/300625  
DATED : August 6, 2019  
INVENTOR(S) : Steven J. Tallarida et al.

Page 1 of 1

It is certified that error appears in the above-identified patent and that said Letters Patent is hereby corrected as shown below:

In the Claims
In Column 29, Line 50, Claim 2 delete "method claim" and insert -- method of claim --, therefor.
In Column 29, Line 63, Claim 3 delete "method claim" and insert -- method of claim --, therefor.
In Column 30, Line 1, Claim 4 delete "method claim" and insert -- method of claim --, therefor.
In Column 30, Line 5, Claim 5 delete "method claim" and insert -- method of claim --, therefor.
In Column 30, Line 9, Claim 6 delete "method claim" and insert -- method of claim --, therefor.
In Column 30, Line 12, Claim 7 delete "method claim" and insert -- method of claim --, therefor.
In Column 30, Line 18, Claim 8 delete "method claim" and insert -- method of claim --, therefor.
In Column 30, Line 23, Claim 9 delete "method claim" and insert -- method of claim --, therefor.
In Column 30, Line 27, Claim 10 delete "method claim" and insert -- method of claim --, therefor.
In Column 30, Line 31, Claim 11 delete "method claim" and insert -- method of claim --, therefor.
In Column 30, Line 34, Claim 12 delete "method claim" and insert -- method of claim --, therefor.
In Column 31, Line 20, Claim 14 delete "method claim" and insert -- method of claim --, therefor.
In Column 31, Line 33, Claim 15 delete "method claim" and insert -- method of claim --, therefor.
In Column 32, Line 1, Claim 16 delete "method claim" and insert -- method of claim --, therefor.
In Column 32, Line 5, Claim 17 delete "method claim" and insert -- method of claim --, therefor.
In Column 32, Line 9, Claim 18 delete "method claim" and insert -- method of claim --, therefor.
In Column 32, Line 12, Claim 19 delete "method claim" and insert -- method of claim --, therefor.
In Column 32, Line 18, Claim 20 delete "method claim" and insert -- method of claim --, therefor.
In Column 32, Line 23, Claim 21 delete "method claim" and insert -- method of claim --, therefor.
In Column 32, Line 27, Claim 22 delete "method claim" and insert -- method of claim --, therefor.
In Column 32, Line 31, Claim 23 delete "method claim" and insert -- method of claim --, therefor.
In Column 32, Line 34, Claim 24 delete "method claim" and insert -- method of claim --, therefor.

Signed and Sealed this
Twelfth Day of November, 2019

Andrei Iancu
*Director of the United States Patent and Trademark Office*